(12) United States Patent
Winkelman et al.

(10) Patent No.: US 9,602,777 B2
(45) Date of Patent: *Mar. 21, 2017

(54) SYSTEMS AND METHODS FOR ANALYZING BODY FLUIDS

(75) Inventors: James Winkelman, Chestnut Hill, MA (US); Milenko Tanasijevic, West Newton, MA (US); David Zahniser, Wellesley, MA (US); James Linder, Omaha, NE (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 328 days.

This patent is subject to a terminal disclaimer.

(21) Appl. No.: 12/768,633

(22) Filed: Apr. 27, 2010

(65) Prior Publication Data

US 2011/0070606 A1    Mar. 24, 2011

Related U.S. Application Data

(63) Continuation-in-part of application No. 12/430,885, filed on Apr. 27, 2009, now Pat. No. 9,017,610.

(Continued)

(51) Int. Cl.
*G01N 1/31* (2006.01)
*G01N 1/38* (2006.01)
(Continued)

(52) U.S. Cl.
CPC ............. *H04N 7/18* (2013.01); *G01N 1/2813* (2013.01); *G01N 1/312* (2013.01); *G06K 9/00* (2013.01);
(Continued)

(58) Field of Classification Search
None
See application file for complete search history.

(56) References Cited

U.S. PATENT DOCUMENTS 3,851,156 A * 11/1974 Green ................ G06K 9/00127
327/355
3,888,206 A    6/1975 Faulkner
(Continued)

FOREIGN PATENT DOCUMENTS

DE        3503475        8/1985
EP        0810428        12/1997
(Continued)

OTHER PUBLICATIONS

Meyer, E., "Vickers Continuous Film", *Cytology Automation: Proceedings of Second Tenovus Symposium*, Cardiff $24^{th}$-$25^{th}$, pp. 147-153 (Oct. 1968).
(Continued)

*Primary Examiner* — P. Kathryn Wright
(74) *Attorney, Agent, or Firm* — Fish & Richardson P.C.

(57) ABSTRACT

Systems and methods analyzing body fluids contain cells including blood, bone marrow, urine, vaginal tissue, epithelial tissue, tumors, semen, and spittle are disclosed. The systems and methods utilize an improved technique for applying a monolayer of cells to a slide and generating a substantially uniform distribution of cells on the slide. Additionally aspects of the invention also relate to systems and method for utilizing multi-color microscopy for improving the quality of images captured by a light receiving device.

29 Claims, 9 Drawing Sheets

Related U.S. Application Data

(60) Provisional application No. 61/047,920, filed on Apr. 25, 2008, provisional application No. 61/173,186, filed on Apr. 27, 2009.

(51) Int. Cl.
　　*H04N 7/18*　　　　(2006.01)
　　*G01N 1/28*　　　　(2006.01)
　　*G06K 9/00*　　　　(2006.01)
　　*G01N 35/00*　　　　(2006.01)
　　*G01N 15/14*　　　　(2006.01)

(52) U.S. Cl.
　　CPC ... *G01N 15/1475* (2013.01); *G01N 35/00029* (2013.01)

(56) References Cited

U.S. PATENT DOCUMENTS

| | | | |
|---|---|---|---|
| 3,985,096 A | 10/1976 | Guimbretiere | |
| 4,175,859 A | 11/1979 | Hashizume et al. | |
| 4,207,554 A | 6/1980 | Resnick et al. | |
| 4,285,907 A | 8/1981 | Hugemann et al. | |
| 4,362,386 A | 12/1982 | Matsushita et al. | |
| 4,395,493 A | 7/1983 | Zahniser et al. | |
| 5,123,055 A | 6/1992 | Kasdan | |
| 5,209,903 A | 5/1993 | Kanamori et al. | |
| 5,338,688 A | 8/1994 | Deeg et al. | |
| 5,419,279 A | 5/1995 | Carrico, Jr. et al. | |
| 5,436,978 A | 7/1995 | Kasdan | |
| 5,625,705 A | 4/1997 | Recht | |
| 5,650,332 A | 7/1997 | Gao et al. | |
| 5,665,309 A | 9/1997 | Champseix | |
| 5,665,312 A | 9/1997 | Sperber et al. | |
| 5,676,910 A | 10/1997 | Levine et al. | |
| 5,741,554 A | 4/1998 | Tisone | |
| 5,743,960 A | 4/1998 | Tisone | |
| 5,766,549 A | 6/1998 | Gao et al. | |
| 5,804,145 A | 9/1998 | Gao et al. | |
| 5,807,522 A | 9/1998 | Brown et al. | |
| 5,882,933 A | 3/1999 | Li et al. | |
| 6,132,353 A | 10/2000 | Winkelman et al. | |
| 6,150,173 A | 11/2000 | Schubert | |
| 6,151,405 A | 11/2000 | Douglass et al. | |
| 6,258,322 B1 | 7/2001 | Meikle | |
| 6,269,846 B1 | 8/2001 | Overbeck et al. | |
| 6,287,791 B1 | 9/2001 | Terstappen et al. | |
| 6,319,470 B1 | 11/2001 | Lefevre et al. | |
| 6,350,613 B1 | 2/2002 | Wardlaw et al. | |
| 6,398,705 B1 | 6/2002 | Grumberg et al. | |
| 6,519,355 B2 | 2/2003 | Nelson | |
| 6,553,135 B1 | 4/2003 | Douglass et al. | |
| 6,576,295 B2 | 6/2003 | Tisone | |
| 6,590,612 B1 | 7/2003 | Rosenqvist | |
| 6,711,283 B1 | 3/2004 | Soenksen | |
| 6,718,053 B1 | 4/2004 | Ellis et al. | |
| 6,869,570 B2 | 3/2005 | Wardlaw | |
| 6,902,703 B2 | 6/2005 | Marquiss | |
| 7,006,674 B1 | 2/2006 | Zahniser et al. | |
| 7,025,933 B2 | 4/2006 | Ganz et al. | |
| 7,105,081 B2 | 9/2006 | Gascoyne et al. | |
| 7,105,295 B2 | 9/2006 | Bass et al. | |
| 7,190,818 B2 | 3/2007 | Ellis et al. | |
| 7,297,311 B2 | 11/2007 | Tamura et al. | |
| 7,300,804 B2 | 11/2007 | Sellek-Prince | |
| 7,368,080 B2 | 5/2008 | Tamura et al. | |
| 7,561,329 B2 | 7/2009 | Zahniser et al. | |
| 7,587,078 B2 | 9/2009 | Zahniser et al. | |
| 7,608,220 B2 | 10/2009 | Jin et al. | |
| 7,689,038 B2 | 3/2010 | Zahniser | |
| 7,716,303 B2 | 5/2010 | Moriez | |
| 7,790,107 B2 | 9/2010 | Nakaya | |
| 7,796,797 B2 | 9/2010 | Nakaya et al. | |
| 7,820,381 B2 | 10/2010 | Lemme et al. | |
| 7,833,485 B2 | 11/2010 | Higuchi et al. | |
| 7,881,532 B2 | 2/2011 | Zahniser | |
| 7,903,241 B2 | 3/2011 | Wardlaw et al. | |
| 7,929,121 B2 | 4/2011 | Wardlaw et al. | |
| 7,929,122 B2 | 4/2011 | Wardlaw et al. | |
| 8,058,010 B2 | 11/2011 | Erickson et al. | |
| 8,081,303 B2 | 12/2011 | Levine | |
| 8,263,414 B2 | 9/2012 | Pugia et al. | |
| 8,284,384 B2 | 10/2012 | Levine | |
| 8,361,799 B2 | 1/2013 | Levine | |
| 2002/0049391 A1 | 4/2002 | Kuracina et al. | |
| 2002/0086431 A1 | 7/2002 | Markham et al. | |
| 2002/0159919 A1 | 10/2002 | Churchill et al. | |
| 2004/0131758 A1 | 7/2004 | Jung et al. | |
| 2004/0175832 A1 | 9/2004 | Hui et al. | |
| 2005/0003458 A1 | 1/2005 | Moore et al. | |
| 2005/0003464 A1 | 1/2005 | Tibbe et al. | |
| 2005/0025672 A1 | 2/2005 | Nakaya et al. | |
| 2005/0058330 A1 | 3/2005 | Mitsuhashi et al. | |
| 2005/0212837 A1 | 9/2005 | Nakagawa et al. | |
| 2006/0051241 A1 | 3/2006 | Higuchi et al. | |
| 2006/0144331 A1 | 7/2006 | Hanafusa et al. | |
| 2006/0223172 A1 | 10/2006 | Bedingham et al. | |
| 2006/0245630 A1 * | 11/2006 | Zahniser et al. ............. 382/133 |
| 2006/0263902 A1 | 11/2006 | Pugia et al. | |
| 2007/0128073 A1 | 6/2007 | Tappen | |
| 2008/0210894 A1 | 9/2008 | Ahn et al. | |
| 2008/0318305 A1 | 12/2008 | Angros | |
| 2009/0032583 A1 | 2/2009 | Lapstun et al. | |
| 2009/0069639 A1 | 3/2009 | Linssen et al. | |
| 2009/0155841 A1 | 6/2009 | Yamasaki | |
| 2009/0162862 A1 | 6/2009 | Merz | |
| 2009/0191585 A1 | 7/2009 | Yamada et al. | |
| 2009/0233331 A1 | 9/2009 | Ostgaard et al. | |
| 2009/0269799 A1 | 10/2009 | Winkelman et al. | |
| 2009/0275076 A1 | 11/2009 | Knesel et al. | |
| 2010/0054575 A1 | 3/2010 | Zhou et al. | |
| 2010/0080440 A1 * | 4/2010 | Yamada ............... G01N 35/026 |
| | | | 382/133 |
| 2010/0111399 A1 | 5/2010 | Ramirez et al. | |
| 2010/0284602 A1 | 11/2010 | Winkelman et al. | |
| 2011/0014645 A1 | 1/2011 | Winkelman et al. | |
| 2012/0147357 A1 | 6/2012 | Wardlaw | |
| 2013/0070077 A1 | 3/2013 | Winkelman | |

FOREIGN PATENT DOCUMENTS

| | | | |
|---|---|---|---|
| EP | 0 861 431 | 3/2000 | |
| EP | 1387171 | 2/2004 | |
| EP | 1804046 | 7/2007 | |
| EP | 1 812 799 | 8/2007 | |
| EP | 1 957 205 | 8/2008 | |
| EP | 2 072 993 | 6/2009 | |
| EP | 2083375 | 7/2009 | |
| EP | 2 202 523 | 6/2010 | |
| GB | 1 349 379 | 4/1974 | |
| JP | 1985-162955 | 8/1985 | |
| JP | 07-020650 | 1/1995 | |
| JP | 07-083817 | 3/1995 | |
| JP | 11-326208 | 11/1999 | |
| JP | 2001-174456 | 6/2001 | |
| JP | 2001-518186 | 10/2001 | |
| JP | 2002-516982 | 6/2002 | |
| JP | 2005-000573 | 1/2005 | |
| WO | WO 97/18457 | 5/1997 | |
| WO | WO 97/26541 | 7/1997 | |
| WO | WO 99/44593 | 9/1999 | |
| WO | WO 01/04276 | 1/2001 | |
| WO | WO 2005/080940 | 9/2005 | |
| WO | WO 2005080940 A1 * | 9/2005 | ......... G01N 33/5094 |
| WO | WO2006127631 | 11/2006 | |
| WO | WO 2007/067847 | 6/2007 | |
| WO | WO 2007/105198 | 9/2007 | |
| WO | WO 2008/046292 | 4/2008 | |

(56) References Cited

FOREIGN PATENT DOCUMENTS

| WO | WO 2008/140969 | * | 11/2008 |
|----|----------------|---|---------|
| WO | WO 2009/033128 |   | 3/2009  |

OTHER PUBLICATIONS

Bacus, J., "Erythrocyte Morphology and Centrifugal 'Spinner' Blood Film Preparations", *The Journal of Histochemistry and Cytochemistry*, vol. 22:506-516 (1974).
Seiter, C., et al., "Contact Angles: New Methods and Measurements", *American Laboratory*, p. 26 (Feb. 2002).
Aller, R., et al., "High Volume Hematology Analyzers: Getting Better All the Time", *CAP Today*, pp. 27-34 (Dec. 2000).
Lehman, C., et al., "Image Technology and its Role in Hematology", *Advance/Laboratory*, pp. 84-88 (May 2000).
Promotional materials for DRD™ Diluter Corporation's Little Squirt™, NanoBlast-96™, and Differential NanoPipettor™/Diluter.
Ward, P., "The CBC at the Turn of the Millenium: An Overview", *Clinical Chemistry*, vol. 46:1215-1220 (2000).
Novis, D., et al., "Laboratory Productivity and the Rate of Manual Peripheral Blood Smear Review: A College of American Pathologists Q-Probes Study of 95141 Complete Blood Count Determinations Performed in 263 Institutions", *Archives of Pathology and Laboratory Medicine*, vol. 130:596-601 (2006).
Walters, J., et al., "Performance Evaluation of the Sysmex XE-2100 Hematology Analyzer", *Laboratory Hematology*, vol. 6:83-92 (2000).
Walker, T., "Comparative Evaluation of the Iris iQ200 Body Fluid Module with Manual Hemacytometer Count", *American Journal of Clinical Pathology*, vol. 131:333-338 (2009).
Brochure—Iris Diagnostics Case Study: New Automated Urinalysis Workcell Review.
Rogers, C., "Blood Sample Preparation for Automated Differential Systems", *American Journal of Medical Technology*, vol. 39: 435-442 (1973).
De Cresce, Robert P. et al., "PAPNET™ Cytological Screening System," *Laboratory Medicine* 22(4): 276-280 (1991).
Office Action in U.S. Appl. No. 12/785,314, dated Oct. 12, 2012.
Bacus and Weens, "An automated method of differential red blood cell classification with application to the diagnosis of anemia," *J Histochem Cytochem.*, 25(7):614-632, Jul. 1977.
Bacus et al., "Image processing for automated erythrocyte classification," *J Histochem Cytochem.*, 24(1):195-201, Jan. 1976.
Bacus, "Cytometric approaches to red blood cells," *Pure Appl Chem.*, vol. 57:593-598 (1985).
Bacus, "Digital image processing measurements of red blood cell size and hemoglobin content ," *Advances in Hematological Methods: The Blood Count*, Chapter 14, 158-181 (1982).
Bacus, "Quantitative morphological analysis of red blood cells," *Blood Cells*, 6(3):295-314, 1980.
Bacus, "Quantitative Red Cell Morphology," Monogr. Clin. Cytol. 9: 1-27 (1984).
Daoust, "The clinical detection of variations in the concentrations of normal leukocyte types: a laboratory comparison of 100-cell manual differential counts on wedge smears and 500-cell counts by the ADC500," *Blood Cells*, 6(3):489-496, 1980.
Zahniser et al., "Detecting infection-related changes in peripheral blood smears with image analysis techniques," *Anal Quant Cytol.*, 5(4):269-274, Dec. 1983.

Zahniser et al., "Spectral bandwidth in automated leukocyte classification," 521, *Cytometry*, 7(6):518-521, Nov. 1986.
Advisory Action in U.S. Appl. No. 12/430,885, dated Jul. 19, 2012, 3 pages.
English translation of the Written Opinion of the International Searching Authority for PCT/CN2007/002665 dated Nov. 15, 2007, 5 pages.
International Preliminary Report on Patentability for PCT Application No. PCT/US2010/032612, dated Nov. 1, 2011, 2 pages.
International Preliminary Report on Patentability for PCT/US2009/041858, issued Feb. 28, 2012, 6 pages.
International Preliminary Report on Patentability for PCT/US2011/021546 mailed Aug. 1, 2013, 7 pgs.
International Search Report and the Written Opinion for PCT/US2009/041858, dated Aug. 10, 2010 (14 pages).
International Search Report and Written Opinion for PCT/US2010/032612, dated Jun. 28, 2010, 11 pages.
International Search Report and Written Opinion for PCT/US2011/021546, mailed Oct. 10, 2011, 10 pages.
Office Action in U.S. Appl. No. 12/430,885 mailed Jan. 13, 2014, 7 pages.
Office Action in U.S. Appl. No. 12/430,885 mailed May 8, 2013, 18 pages.
Office Action in U.S. Appl. No. 12/430,885, dated Apr. 12, 2012, 21 pages.
Office Action in U.S. Appl. No. 12/430,885, dated Sep. 30, 2011, 23 pages.
Office Action in U.S. Appl. No. 12/785,314 mailed Apr. 30, 2013, 18 pages.
Office Action in U.S. Appl. No. 12/785,337 mailed Nov. 21, 2013, 24 pages.
Office Action in U.S. Appl. No. 13/619,381, mailed Jan 15, 2014, 7 pages.
Office Action in U.S. Appl. No. 13/619,381, mailed May 9, 2013, 16 pages.
Restriction Requirement in U.S. Appl. No. 12/430,885, dated May 27, 2011, 10 pages.
Brochure—Iris Diagnostics Case Study: New Automated Urinalysis Workcell Review (2009).
Promotional materials for DRD™ Diluter Corporation's Little Squirt™ (Jan. 7, 2008).
Promotional materials for NanoBlast-96TM (Feb. 28, 2006).
Promotional materials for Differential NanoPipettorTM/Diluter, small volume sampling (Feb. 28, 2006).
Promotional materials for Differential NanoPipettorTM/Diluter (Apr. 9, 2005).
Office action mailed Nov. 26, 2013 in related U.S. Appl. No. 12/785,314, 41 pgs.
Gelemsa et al., "Procedures for the Automation of the White Blood Cell Differential Count," NTG/GI Gesellschaft fur Informatik Nachwichtentechnische Gesellschaft Fachtagung "Cognitive Verfahren und Systeme", Springer-Verlag, Berlin (1973) pp. 237-256.
Cornet et al., "Performance Evaluation and Relevance of the Cellavision DM96 System in Routine Analysis and in Patients With Malignant Hematological Diseases," *International Journal of Laboratory Hematology*, vol. 30 (2007) pp. 536-542.
Wright's Stain definition, downloaded from http://medical-dictionary.thefreedictionary.com/Wright's+stain on Nov. 15, 2013.
Gulati et al., "Criteria for Blood Smear Review," *Laboratory Medicine*, vol. 33, No. 5 (2002) pp. 374-377.

* cited by examiner

SYSTEMS AND METHODS FOR ANALYZING BODY FLUIDS

PRIORITY CLAIM

This application claims the benefit of priority to U.S. Provisional Application 61/173,186; filed Apr. 27, 2009. This application is a continuation-in-part of U.S. Ser. No. 12/430,885; filed Apr. 27, 2009; which claims the benefit of priority to U.S. Provisional Application 61/047,920; filed Apr. 25, 2008.

FIELD OF THE INVENTION

This invention relates to a system and process for determining composition and components of fluids. More specifically the present invention provides improved techniques for viewing cellular morphology, and determining the number of a particular type of cell in a portion of a body fluid.

BACKGROUND OF THE INVENTION

Pathology is a field of medicine where medical professionals determine the presence, or absence of disease by methods that include the morphologic examination of individual cells that have been collected, fixed or air-dried, and then visualized by a stain that highlights features of both the nucleus and the cytoplasm. The collection of the cells often involves capturing a portion of a person's body fluid, placing the body fluid on a slide, and viewing the fluid on the slide using a microscope.

One of the most commonly performed pathologic studies is the CBC (the Complete Blood Count). To perform a CBC, a sample of blood is extracted from a patient and then the cells are counted by automated or manual methods. The CBC is commonly performed by using an instrument, based on the principal of flow cytometry, which customarily aspirates anticoagulated whole blood and divides it into several analysis streams. Using the flow cytometer a number of primary and derived measurements can be determined including: i) red blood cell (RBC) count, hemoglobin (Hb), hematocrit (Hct), red blood cell indices (mean corpuscular volume, MCV, mean corpuscular hemoglobin, MCH and mean corpuscular hemoglobin concentration MCHC), red blood cell distribution width, enumeration of other red blood cells including reticulocytes and nucleated red blood cells, and red blood cell morphology; ii) white blood cell (WBC) count and WBC "differential" count (enumeration of the different normal white blood cell types, including neutrophils, lymphocytes, eosinophils, basophils and monocytes, and the probable presence of other normal and abnormal types of WBC that are present in various disease conditions); iii) platelet count, platelet distribution widths and other features of platelets including morphological features; and iv) other abnormal cells or other unusual cells or cellular components that may be in circulating blood. In flow cytometers, red blood cell, WBC, and platelet morphological characterizations are typically made indirectly, based on light absorption and light scattering techniques and/or cytochemically based measurements. Some advanced flow cytometers calculate secondary and tertiary measurements from the primary measurements.

Flow based CBC instruments generally require extensive calibration and control, maintenance, and skilled operators, and they have substantial costs associated with acquisition, service, reagents, consumables and disposables. One significant problem with these systems in routine use is that a large proportion of blood specimens require further testing to complete the assessment of the morphologic components of the CBC. This involves placing a sample of blood on a slide, smearing the sample against the slide to form a wedge smear, and placing the slide under a microscope. This process is often done manually by skilled medical technologists, which increases the cost and time to receive results from the tests. The direct visualization of blood cells on a glass slide must be performed whenever the results of the automated test require further examination of the blood sample. For example, a "manual" differential count is performed by direct visualization of the cells by an experienced observer whenever nucleated immature RBCs are found or WBCs suspicious for infection, leukemias or other hematologic diseases are found.

The proportion of these specimens requiring further review generally ranges from 10% to 50%, depending on the laboratory policy, patient population and "flagging" criteria, with a median rate of around 27%. The most frequent reasons for retesting include the presence of increased or decreased number of WBCs, RBCs or platelets, abnormal cell types or cell morphology, clinical or other suspicion of viral or bacterial infections.

In addition to additional work involved in performing manual differential counts, this process has a number of additional technical limitations. These include distortions of cell morphology because of mechanical forces involved in smearing the cells onto the slide, and cells overlapping one another, which makes visualization of individual cell morphology difficult.

Cytopathology is a subspecialty of pathology where medical professionals determine the presence, or absence of disease by the morphologic examination of individual cells that have been collected, fixed or air-dried, and then stained by a unique stain that highlights features of both the nucleus and the cytoplasm.

Examples of cytologic examination include the assessment of cells collected from the uterine cervix (The Pap Test), evaluation of urine samples for bladder cancer, assessment of lung samples for the presence of cancer or inflammatory diseases, assessment of aspirates from potential tumor sites, or the evaluation of samples collected from effusions in body cavities.

Cells that are collected for cytologic examination may be directly smeared onto a glass microscope slide, they may be deposited onto the slide by centrifugation, they may be collected by a filtration method, or they may be concentrated by liquid-based cytology methods such as the ThinPrep or SurePath methods. These approaches used different types of preservative solutions that typically are alcohol-based, and attempt to deposit the cells to preserve cell morphology.

There are several limitations to current cytologic preparation methods. These include distortions of cell morphology because of mechanical forces involved in smearing or sedimenting the cells onto the slide. The deposition of cells onto the slide may result in cells overlapping one another, so that individual cell morphology cannot be visualized. Additional limitations associated with current cytologic preparation methods include, although are not limited to, the following: inhomogeneous sampling of a specimen due to differential rates of sedimenting cells onto a slide; the loss of cell clusters during certain types of preparation methods; the loss of small cells in methods that depend on density gradient methods of preparation; damage or nonspecific loss of inflammatory cells in centrifugation methods; and the inability to determine the absolute number of cell types in a sample, which may be important in determining the number of abnormal cells in a sample or in counting the number of inflammatory cells to determine the predominant type of inflammation that is in a sample.

Examples of these limitations are found with the Pap testing techniques that may not adequately display certain cell clusters because of smearing or filtration processes used to prepare the slide. The density gradient preparation method employed by the SurePath method may not capture small, buoyant cells that float atop the gradient. Centrifugation methods may result in the inconsistent loss of small lymphocytes, which can be problematic when an accurate differential count of inflammatory cells is required. Certain types of inflammatory lung diseases, such as idiopathic pulmonary fibrosis and sarcoidosis are characterized by unique profiles of inflammation that can only be useful diagnostically if an accurate enumeration of those cells can be determined.

A method of preparation of cytology samples that would not distort morphology, and that would result in a homogeneous and quantifiable number of cells being placed on the slide would overcome the limitations of current preparation methods.

Other examples involving body fluids include the detection of cells or cellular components that may be circulating in the peripheral blood. For example, cells from a non-hematological tumor may be found in the blood and could be detected by visual examination or automated examination of a slide. Special markers such as antibodies may be used to tag these cells. Other cellular components such as specific proteins may also be present in the blood either intracellularly or extracellularly and could be evaluated on the slide, typically by using certain markers to tag these slides. Certain inclusions in blood cells may also be detectable; for example parasites.

SUMMARY OF THE INVENTION

The present invention provides improved systems and methods for preparing and applying cells from a body fluid on a slide. Additionally systems and methods for imaging the cells are provided. The images may be later used to perform tests including image-based counting and assessment of the morphology of the cells. The present invention may be used on a variety cells from body fluid including blood, bone marrow, urine, vaginal tissue, epithelial tissue, tumors, semen, spittle, and other fluids.

By way of example, in the case of analyzing blood or bone marrow, aspects of the present invention may used process a slide and optionally capture an image of the slide. The image may be later used for performing various tests that provide for a count of various cell types, or an assessment of the morphology of the cells. One example is a complete blood count including image-based counting and assessment of the morphology of the formed elements of blood, including RBCs, WBCs, and platelets. Embodiments of the present invention may improve the accuracy of the CBC as a result of direct visualization of the formed elements of blood. The use of the disclosed systems and processes for applying a monolayer of cells onto a slide enables assessment of certain cell types, particularly of abnormal and immature WBCs that are found in cases of abnormal bone marrow function including hematological malignancies. Further, the present invention may decrease costs associated with instrumentation; decrease cost of consumables and reagents; and require less operator time and reagents, fewer repeated tests, and fewer moving parts. It may also reduce the turnaround time for many of the CBC tests that currently require visualization of blood cells after the instrumental portion of the test is completed, by allowing cells to be visualized on a monitor instead of under a microscope.

Aspects of the present invention are effective at preserving cell morphology. This may be important for patients with hematological malignancies such as chronic lymphocytic leukemia (CLL) or acute myeloid leukemia (AML). The systems and processes for creating a monolayer of cells from body fluid may enable detection of a larger number of morphologically well preserved blast cells and other immature or fragile cells. This would allow their more accurate recognition at an earlier stage of the leukemic or other disease process. Certain aspects of the present invention provide for preparing a substantially uniform distribution of cells across a test area of a slide.

Aspects of this invention may relate to the application of cells from body fluids to a slide and include possibly mixing the cells contained in the body fluid with a diluent, collecting a sub-sample (aliquot) of a known volume from the solution, and then depositing the aliquot onto a substratum such as a slide using a dispensing device or applicator. The cells may be allowed to air dry or may be fixed (using a fixative solution) or both, depending on the examination that is anticipated. The cells may also be stained. The stained cells on the substratum may be counted and examined by an automated imaging system utilizing a computer or viewed by manual microscopic examination. Digital images may be shown on a computer display to reduce the need for manual microscopic review.

Aspects of the invention also relate to systems and methods for collecting cells from a body site, placing the cells into a preservative solution, mixing the cells in the solution to assure a homogeneous distribution, collecting an aliquot of known volume from the preservative solution and then depositing the aliquot onto a slide using an applicator. The cells may be fixed, stained, or allowed to air dry, depending on the examination that is anticipated. The slide containing the specimen may be used for either manual microscopic examination, or be examined by an imaging technique that can enumerate the different types of cells that are present on the slide.

Systems and methods of the present invention provide a number of improvements over prior art techniques. For example, an embodiment of the present invention may be used to determine the number of cells in a sample of the cervix that are infected by the Human Papilloma Virus (this may indicate the viral burden, which is a prognostic factor to assess if an abnormality may progress, remain stable, or regress). Embodiments of the present invention may be able to determine how many viral or infected cells are in the sample. Additionally, certain embodiments of the present invention may be able to determine the differential cell count in an non-gynecologic sample collected from a body cavity effusion. In further embodiments, the system or method could determine that there is a large number of acute inflammatory cells in a sample (which the system or method may use to determine the presence of a bacterial infection). Similarly, if an embodiment of the present invention determined there were a high number of lymphocytes in a particular sample this may suggest a viral infection, autoimmune disease, or tuberculosis.

DETAILED DESCRIPTION OF THE INVENTION

Figure 1A:
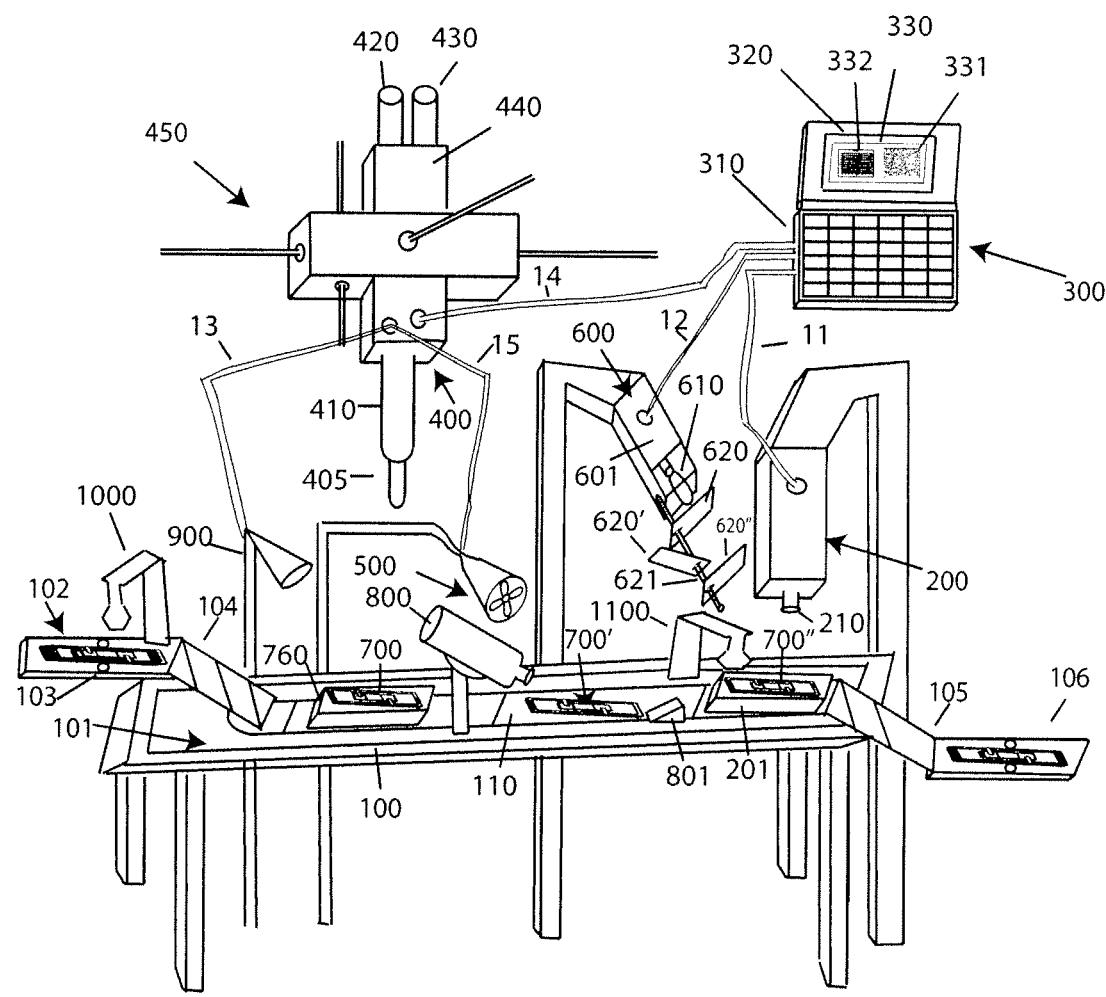
FIG. 1A: is a perspective, schematic view of a system for analyzing body fluids.

With reference to FIG. 1A, a system 10 for analyzing body fluids is disclosed. The system may comprise a platform 100, a light receiving device 200, a computer 300, an applicator 400, a gas circulation device 500, a light source 600, a dispenser 800, a discharge device 900, a slide labeler 1000, and slide label reader 1100. The following sections below include capitalized headings intended to facilitate navigation through the specification, which are not intended to be limiting of the invention in any manner.

The Platform 100

In embodiments that feature a platform 100, an advancer 110 may be configured to receive one or more slide apparatuses 700-700". The advancer 110 may be attached to a surface, such as the top surface 101, of the platform. The advancer 110 may take the form of a belt as shown in FIG. 1A, the system may use a mechanical arm, gravity, magnetism, hydraulics, gears, or other locomotion techniques to move the slide apparatus along the surface 101 of the platform.

The platform 100 may also comprise a feeder 102 and a collector 106 for respectively feeding and collecting the slide apparatuses 700 from or to a stack or rack. The feeder 102 may be equipped with a feeder propulsion mechanism 103 (such as rubberized wheels) for pushing the slides down a ramp 104 onto the advancer 110. (Of course, embodiments of the invention could be built without a ramp, for example, if the feeder is level with advancer 110, no ramp would be needed. Alternatively, a mechanical arm could be used to grab the slide apparatus 700 and place the slide apparatus 700 on the advancer directly.) Alternate mechanisms to propel the slide out of the feeder 102 may be used such as magnets or hydraulics. The feeder may comprise a sensor for determining how many slides are present. The sensor could measure the weight of the slide apparatuses 700 for example to determine how many slide apparatuses were present. FIG. 1A illustrates 3 slide apparatuses 700 stored in the feeder 102. The collector 106 may also comprise a sensor for determining how many slides are present in the collector 106. The sensor may inform the computer when a preset number of slides have been analyzed or may inform the computer of the receipt of a slide on an ongoing basis.

The Light Receiving Device 200

The light receiving device 200 may be a microscope (such as brightfield microscope), a video camera, a still camera, or other optical device which receives light. The light receiving device may comprise an objective, eyepiece, a stage or any combination thereof. In embodiments using a standard brightfield microscope, one containing an automated stage (a slide mover 201) and focus may be selected. In one embodiment, a microscope may be attached to a motorized stage and a focus motor attachment. The microscope may have a motorized nosepiece, for allowing different magnification lenses to be selected under computer 300 control. A filter wheel may allow the computer 300 to automatically select narrow band color filters in the light path. LED illumination may be substituted for the filters, and use of LEDs may reduce the image acquisition time as compared to the time required for filter wheel rotation. In LED and filter wheel embodiments, the light receiving device many contain an autofocus controller for shifting the focal point of the light so that it is focused when it enters the light receiving device. For example, the autofocus controller may control the relative position of an objective or stage of the light receiving device 200 to focus light on a lens of the light receiving device 200. A 1600×1200 pixel firewire camera may be used to acquire the narrow band images.

Figure 3:
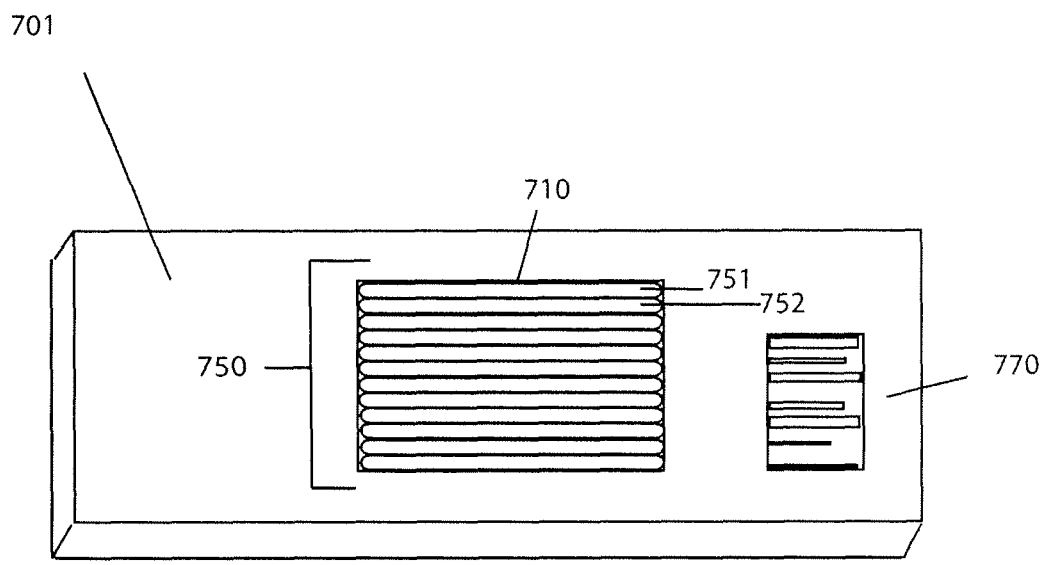
FIG. 3: is an enlarged top view of the slide and slide specimen.
Figure 3:
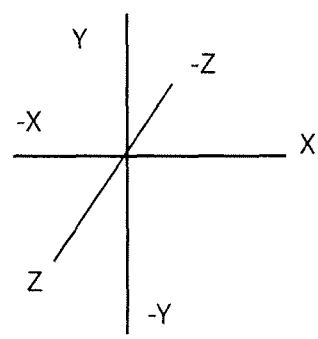

In some cases, the light receiving device will receive light reflected off slide apparatus 700" and store an image of that light. However, since the light emission source 600' can be positioned below the platform 100, the light emission source may direct light so that it passes through the platform 100 and the slide 701 into the light receiving device 200. In some embodiments fluorescent emission from the cellular objects may be detected in the light receiving device 200. The light receiving device may be connected to a computer through a link 11, and may be capable of X, Y, and Z axial movement (in other embodiments a motorized stage or slide mover 201 may provide X, Y, and Z movement.) The light receiving device may comprise a link 11 such as a wire as shown in FIG. 1A, or other wireless systems may be used. The light receiving device 200 and any of the other components may be interfaced with the computer 300 through a link (11-15) which may provide power to the component, provide instructions from the computer 300 to the component, or allow the component to send information to the computer 300. Light receiving device 200 may contain pan, tilt, or locomotive actuators to allow the computer 300 to position the device 200 in an appropriate position. The light receiving device may contain a lens 210 that focuses the light. The light receiving device may capture black and white or color images. Alternatively, two or more light receiving devices could be used to divide the processing time associated with capturing the images. For example, one light receiving device may operate as a low magnification image station while another light receiving device operates as a high magnification image station. Similarly, in some embodiments, the system 10, platform 100, computer 300, or light receiving device 200 may direct a slide mover 201 to move the slide apparatus 700 to store images of all the cells in the slide. Using a slide mover 201 may be desirable, if for example, the field size of the light receiving device 200 is smaller than the specimen zone 710 (FIG. 3).

The Computer 300

The computer 300, may be a laptop as shown in FIG. 1A, or a server, workstation, or any other type of computing device. The computer may comprise a processor, a display 320, an interface 310, and internal memory and/or a disk drive. The computer 300 may also comprise software stored in the memory or on computer readable media such as an optical drive. The software may comprise instructions for causing the computer to operate the light receiving device 200, the applicator 400, the applicator controller 490, the fan 500, the platform 100, advancer 110, light source 600, dispenser 450 or 800, or any component connected to one of these components. Similarly, the computer may receive information from any of these components. For example, the software may control the rate of dispersal of slides from the feeder 102, and feeder 102 may inform the computer about the number of slides present. In addition, the computer 300 may also be responsible for performing the analysis of the images captured by the light receiving device.

In an embodiment of the invention capable of preparing and analyzing cells from blood samples, the computer 300 may be able to calculate the number of a specific type of cell in a particular volume of blood, for example for blood, red cell, white cell, and platelet counts and other measured and derived components of the CBC such as: hemoglobin content, red blood cell morphology, or WBC differential could be calculated. The image analysis software may analyze each individual field and sum the total red and white cell counts. To calculate the total counts per microliter in the patient vial, the number counted on the slide is multiplied by the dilution ratio and volume of the sub-sample. Results of the counts, morphologic measurements, and images of RBCs and WBCs from the slide may be shown on the display 320. In some embodiments, the computer 300 may be able to display numerical data, cell population histograms, scatterplots, and direct assessments of cellular morphology using images of blood cells displayed on the monitor. The ability to display cellular morphology provides users of the system 10, the ability to quickly establish the presence or absence of abnormalities in cell morphology that may warrant preparing an additional slide for manual review by an experienced technician or other professional. The software may provide the computer instructions to display images 331 received from the light receiving device or may cause the display 330 to show the results 332 (in perhaps a chart or graph for example) of an analysis of the images. Similarly, the computer 300 may be able to enumerate the number of cells of a specific type in a particular blood volume or enumerate the number of damaged cells, cancerous cells, or lysed cells in a particular volume of blood. The memory of the computer may contain software to allow the computer to perform the analysis process. The computer may use one or more magnifications during the analysis. While the example above describes using an embodiment of the invention for preparing and analyzing cells from a sample of blood, embodiments of the present invention may be used for preparing and analyzing cells from other fluids such as bone marrow, urine, vaginal tissue, epithelial tissue, tumors, semen, spittle, and/or other body fluids.

Although shown as one component, computer 300 may comprise multiple computers and a first computer could be used for controlling the components and a second computer could be used for processing the images from the light receiving device 200. In some embodiments, the various computers may be linked together to allow the computers to share information. The computer 300 may also be connected to a network or laboratory information system to allow the computer to send and receive information to other computers.

The Applicator 400

In certain embodiments, the applicator 400 may comprise a syringe, a manual or motor driven pipettor or a motor controlled pump attached through a tube to the applicator tip 405. While many different types of pipettes or syringes could be used, test results have shown improved results can be obtained through using an applicator 400 having better than 2% accuracy. The pump may be a peristaltic pump, a syringe pump, or other similar device that allows small volumes of fluid samples containing cells to be aspirated and dispensed through an orifice. Typically such an orifice will be contained in a tip 405 that is two to five millimeters in outside diameter with an inner diameter of 0.5 millimeters. The tip 405 may be disposable or washable. The tip 405 may be rounded to facilitate insertion and cleaning of the tip. Fluid flow through the tip is controlled to allow a thin layer of body fluid containing cells to be deposited onto the slide. By optimizing flow rate through the tip and the relative speed and height of the tip over the slide an appropriate density of cells can be deposited onto the slide. Each of these factors influences the other, so the proper combination of height, flow rate through the tip, and speed over the slide must be determined. In one embodiment the flow rate through the tip is 0.1 microliters per second while the tip is moving at a speed of 30 millimeters per second over the slide surface at a height of about 70 microns. In another embodiment, for example when the body fluid comprises undiluted blood, the flow rate through the tip is approximately 0.04 microliters per second while the tip is moving at a speed relative to a point on the slide of 50 millimeters per second at a height of about 10 microns above the slide surface. The viscosity and consistency of the particular body fluid specimen will influence the flow rate through the tip and the relative speed and height of the tip over slide required to ensure that an appropriate density of cells are deposited on the slide for examination.

In use, the applicator 400 may comprise a known volume of body fluid such as 30 microliters (ul). Some body fluids may need to be pre-processed to disperse cells that may be clumped together or to minimize mucous or other protein material that may cause the cells to stick together. Other body fluids such as urine may need to concentrated before the body fluid is placed into the applicator. The applicator may mix this fluid with a stain or diluent, and eject a portion of this fluid onto the slide apparatus 700 (particularly the specimen zone 710, FIG. 3). A typical sub-sample would be an aliquot of approximately ½ µl to 2 µl, but may be in the range of ¹⁄₁₀ to 10 µl. In some embodiments, the system 10 or applicator 400 may contain a first reservoir 420 for storing the body fluid and a second reservoir 430 for storing diluent. In some embodiments the body fluid will not be diluted.

The system 10 or applicator 400 may contain one or more dispensers 800. The dispenser 800 (or 450 in FIG. 1B) may be used to direct a fixative or a stain onto the slide 701. In this embodiment, the applicator 400 may contain one or more fluid chambers 410 to eject body fluid, diluent, stain, and fixative from the applicator 400. Some dispensers may be able to store both fixative and stain, and direct them sequentially onto the slide, or in alternate embodiments two dispensers may be used (one for the fixative and one for the stain.) Excess stain and fixative may be removed from the slide, by tilting the slide apparatus so that it is orthogonal (or angled) to the platform surface 101. A slide tilter 801 may be used for this purpose. Slide tilter may comprise a simple wedge as shown, or may comprise a mechanical arm to tilt the slide.

In the embodiment shown in FIG. 1A, the stain dispenser is attached to the platform 100. Examples of stains compatible with embodiment shown in FIG. 1A may include: Wright-Giemsa stain, Geimsa stains, and Romanowsky stains. Other solutions that could be dispensed are fixatives (methanol) and buffer solutions. Other visualization methods involving immunocytochemical reagents or other markers of specific cell components may also be used. The stain dispenser may also be embodied as a stain reservoir 450 and attached to the applicator 400 (see FIG. 1B). Examples of stains compatible with the embodiment shown in FIG. 1B may include: Romanowsky stains, reticulocyte stains, and stains using specific antibodies. Additional stains may be used with embodiments of the invention including hematoxylin and eosin; immunocytochemical stains; histochemical stains for viewing cellular components; and antibody, aptamer or other stains based on binding a ligand to an antigen. In the embodiment having dispenser 800, the dispenser can dispense stain onto the slide apparatus (particularly the specimen zone 710.) Dispenser 800 may take the form of a peristaltic pump. In the embodiment having a stain reservoir 450, the stain may be mixed in with the body fluid and the diluent from reservoirs 420 and 430. The body fluid and the diluent may be mixed together by a mixer 440, which can mix the fluid and diluent in certain ratios. In an alternate embodiment, the slide could be immersed into one or more baths of the fixing and staining solutions. In another embodiment, fixing and staining solutions could be moved across the slide using capillary action.

Various fixatives and diluents may be used with the present invention. For example 85% methanol can be used as the fixative. For some stains an ethyl alcohol or formaldehyde based fixative might be used. Diluents useful for diluting whole blood for example, may include salt solutions or protein solutions. Salt solutions range from "physiological saline" (0.9N), to complex mixtures of salts, to the commercial preparation PLASMALYTE® that simulates virtually all the salts found in human blood serum. Protein solutions can range from simple solutions of bovine albumin to PLASMANATE®, a commercial preparation with selected human plasma proteins. Such preparations can vary in protein concentrations, buffers, pH, osmolarity, osmalality, buffering capacity, and additives of various types. Synthetic or "substitute" versions of these solutions may also be usable, including FICOLL® or Dextran or other polysaccharides. Other substitutes may be used. An example of a diluent is Plasmalyte PLASMALYTE® plus PLASMANATE® in the proportion of 4:1 (PLASMALYTE®: PLASMANATE®). Another example of a diluent is 5% albumin. When analyzing whole blood, a dilution of 2 parts blood to 1 part diluent can be used, where the diluent is a physiologically compatible solution, but a range of dilution from 0:1 (no dilution) to 10:1 (diluent:blood) may be used in alternate embodiments.

Embodiments of the present invention may also be used with body fluid samples that require concentration before applying flows of cells from such fluid samples to a slide. For example, body fluids such as urine may require concentration to ensure that the flows of cells placed on the slide contain sufficient quantities of cells onto the slide for analysis. Fluid samples may be concentrated through techniques such as centrifugation, filtration, or use of cell concentration tubes.

The applicator may comprise a hydraulic piston for pushing the fluid out of fluid chamber 410 (like a syringe or a pipette). A tip 405 may be provided for adjusting the flow rate of the fluid. While size of the tip does not affect the speed (ul/sec) in which the solution flows out of the tip, generally, the smaller the opening in the tip, the greater the force generated by the fluid flowing from the tip. Additionally, the size of the tip affects thickness of the fluid flows 750 shown in FIGS. 2 and 3. A tip having a 0.3 millimeter inner diameter may provide for a flow rate of 0.1 microliters per second, and the distance from a middle point 751 of the first flow to the middle point 752 of the second flow may be 500 microns. In order to create the flows 750 shown in FIGS. 2 and 3, the system 10 may be configured to account for the variances in the number of cells in a given body fluid specimen. For example, in human peripheral blood samples, the range is large but within one order of magnitude. In order to accurately count the blood cells, the overlap between red blood cells should be minimized. One method to provide minimal overlapping between cells is to lay down non-touching rows of cells from the tip of the applicator. Increasing viscosity of the diluted fluid or the type or amount of diluent may affect the width of the final settlement positions of the flows 750. By selecting a distance between rows to allow for the typical variation in blood samples, all cells can be counted in all samples. For many samples these gaps will be seen between the flows; however this does not affect the image analysis and the row and gap effect tends not to be noticed during high magnification manual review under the microscope. To avoid these gaps, a light receiving device could be attached to the applicator or positioned near station A (see FIG. 7A) to allow the computer 300 to determine the width of the first flow 751 (FIG. 3) formed by directing the cells onto the slide. By determining the width of the flow, i.e. how far the blood flows sideways from location the fluid was placed on the slide, the computer 300 could cause the applicator to adjust the gap size between the flows. The computer 300 calculates the distance the second flow 752 (FIG. 3) needs to be from the first flow 751, and place the flows so that they settle adjacent to one another minimizing the formation of any gaps between the flows. Using this process, a gapless or contiguous flow of cells can be applied to the specimen zone 710.

To physically place the cells on the slide 701, the computer 300 could direct the applicator controller 490 to perform the body fluid application process 7B (see FIG. 7B) which involves moving the body fluid chamber 410 in the X, Y, or Z directions to position the tip 405 so that it is tracing the eventual locations of the flows 750. In some embodiments, two of the directions may be held fixed, so that the tip 405 moves in a relatively straight path in relation to the slide 701. In other embodiments, one of the directions may be held fixed, so that the tip moves in a wavy, arcuate, or circular path in relation to the slide 701. In still other embodiments all three directions may be modified as the tip 405 is moved in relation to the slide 701. In some embodiments, the X, Y, and Z directions are all perpendicular to each other affording the applicator the ability to move in any direction in a three dimensional coordinate system. In other embodiments, the system moves the slide 701 in the X, Y, or Z directions to position the slide under the tip 405 and move the slide while the tip 405 applies flows of cells from body fluid on the slide.

The computer 300 may be connected to the applicator controller 490 to control this movement. In the embodiment shown in FIG. 3, the controller may position the tip at the top left corner of the specimen zone 710 and proceed to place fluid sample onto the slide by dispensing the fluid from the fluid chamber 410. As the tip dispenses fluid, the controller 490 may move the tip in the positive X direction to the top right portion of the specimen zone 710 (see FIG. 3). Once the top right section is reached, the controller 490 may move the tip in the negative Y direction one flow width. The flow 750 width may range from 300 to 1000 microns, and flow thickness increases as the flow rate of fluid out of the tip increases and/or the speed of the tip across the slide decreases. Additionally the viscosity of the fluid and diluent choice may affect the width of the flow 750 (FIG. 3). Typically, the cells of the fluid will settle within a few seconds once placed on the slide. Once the tip has been moved one flow width, the controller may move the tip in the negative X direction to the leftmost side of the specimen zone 710. Once the leftmost side is reached, the tip again may be moved one flow width in the negative Y direction. This process may be repeated until the entire specimen zone is covered or until a specific quantify of body fluid has been dispensed on the slide such as one microliter. In alternate embodiments, the diluted body fluid could be applied to slide with a fixed applicator and slide which moves via the moveable slide controller 760 (this application process 7A is shown on FIG. 7A.) The slide controller 760 may be moveable in the X, Y, Z direction to move the slide apparatus in similar positions to allow the applicator to place flows 750 of body fluid on the specimen zone 710.

Figure 4:
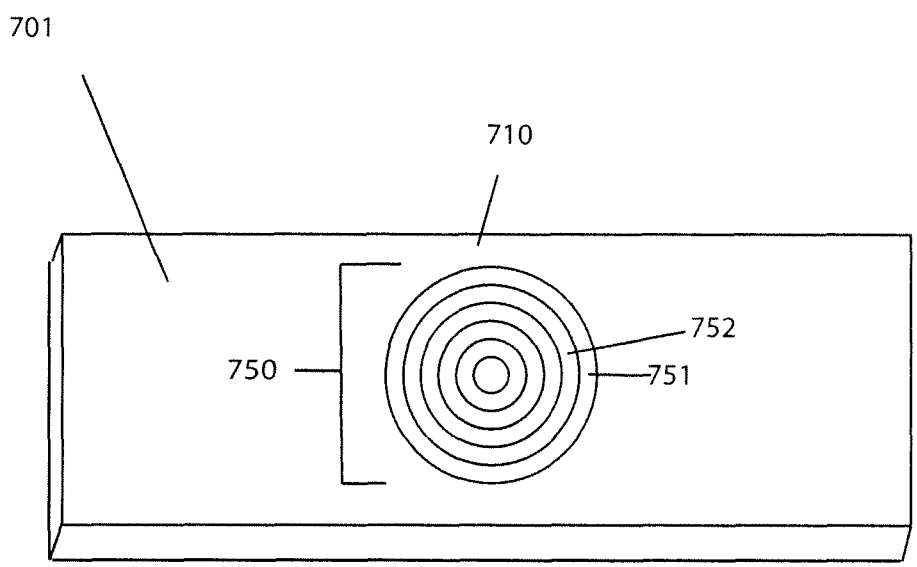
FIG. 4: is an alternate embodiment of the top view of the slide and slide specimen.
Figure 4:
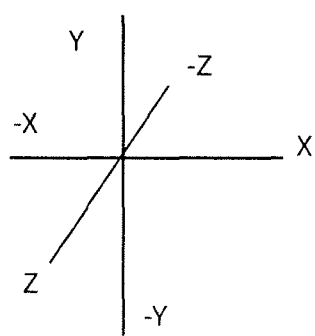

The number of cells placed on the slide 701 using this method will vary depending on the type of body fluid being examined and the dilution ratio. Assuming whole blood were being analyzed with a 1:3 ratio (blood:diluent), about 900,000 red blood cells, 45,000 platelets, and 1,000 white blood cells would be placed on the slide. Though FIG. 3 shows the generation of a uniformly distributed fluid specimen in a rectangular shape, other shapes may be constructed in a similar manner. FIG. 4, shows for example, a fluid flow comprising a plurality of concentric circles. Like FIG. 3, the fluid flows 750 are placed adjacent to one another to create a uniform viewing field. This process provides a highly uniform distribution of cells across the specimen zone 710, facilitating the analysis process. Additionally, the computer 300 can alter the appearance and width of the fluid on the zone 710. For example, the computer 300 may control the speed at which the tip moves across the specimen zone, which would affect the thickness of the fluid resting on the zone. In some embodiments, speeds of 10 to 100 mm/s may be selected in order to provide the zone with a specimen which is about one cell thick. The controller 490 also may select the height of the tip above the slide 700. A height of 70+/−40 microns above the slide may be used in order to minimize damage to fluid cells when they come into contact with the slide apparatus 700, and to maintain fluid flow from the tip to the substrate.

The Gas Movement Device 500

Gas movement device 500 may comprise a fan (such as shown in FIG. 1) or may comprise other gas movement devices such as a compressor or a bellow for example. Gas movement device 500 may be connected directly to the computer 300 or may be connected through another component such as the platform 100 or the applicator 400 (as shown.) The gas movement device pushes gas (in some cases atmospheric air) across the slide to control the rate at which the slide dries. Moving too much air too quickly (i.e. too high of a fan speed) across the slide can cause cells in the specimen to burst due to excessively rapid drying, and too little air too slowly (i.e. too low of a fan speed) across the slide can cause the cells to dry too slowly and appear to shrink. The computer 300 may select the amount of air that moves across the slide in a period of time (i.e. the cubic feet of air per second) based upon the distance the gas movement device is from the slide, the type of fluid being analyzed, the relative humidity, the width of the flows, and averages thickness of the flows (this would be the amount of cells in each flow in the Z direction). The gas movement device 500 may be placed near the slide apparatus 700, and positioned so that the device directs gas to strike the slide at an angle of 30-60° angle (45° degrees can be used) for a period of about 15 to 20 seconds. In some embodiments, the computer can control of humidity and temperature settings in the vicinity of the system to allow the drying process to occur without the use of a gas movement device 500.

The Light Emission Device 600

Two different embodiments of light emission device 600 are illustrated. In FIG. 1A, light emission device 600 comprises a housing 601, a multispectrum light source 610, a number of light filters 620, 620', and 620", and a filter selector 621. As shown in FIG. 1A, a portion of the housing has been removed to better show the light source 610. Light source 610 may comprise a white light source or other multispectrum light source such as a halogen bulb, florescent bulb, or incandescent bulb etc. Filters 620-620" may be used to filter the multispectrum light into a single wavelength or a narrow band of wavelengths. The filter selector 621 may select which filters appear in front of the light source 610. In some embodiments more than one filter may be used to allow a particular range of light to illuminate the slide. Filter selector 621, may comprise a rotation motor and a rod to spin the filters in and out of the path of the light. In a second embodiment light source may comprise one or more lasers or LEDs (630) which emit a narrow band of light (see FIG. 1B). An advantage for using LEDs in this system 10, is that LEDs can rapidly be switched on and off, allowing the light receiving device, for example a single black and white camera, to acquire the multiple spectral images in a very short time. LEDs also produce narrow bandwidths of illumination, typically from 15 to 30 nm full width at half maximum (the breadth of the wavelength intensity distribution at half of the peak brightness of the maximum intensity). Also, LEDs in the visible range do not project heat-producing infrared energy into the optical system and are relatively long lived as compared to conventional lamps. An advantage of using narrow-band illumination rather than unfiltered white light (i.e. broad-band illumination) is that using narrow band illumination increases the sharpness of the images generated by the light receiving device 200. If the light receiving device 200 contains a lens, the presence of the lens may cause some chromatic aberration that results in slight focus shifts or image quality degradation when using different colors. With white light illumination this can result in an overall degradation of the image quality. The light receiving device 200 may capture a black and white image for each narrow-band of illumination. The computer 300 may correct focus and image quality for each wavelength by adjusting the focal distance or the distance of the lens from the slide. In some embodiments, the computer 300 may shift the focus position of the lens while a number of light colors are emitted sequentially to improve the quality of the image.

Various wavelengths of light may be directed by the light emission device 600. Two to eight or more different wavelengths of light may be directed at the slide apparatus 700. For example, wavelengths of approximately 405-430 nm are useful for imaging a hemoglobin-only image for assessing RBC morphology and hemoglobin content. Using an image taken with such a wavelength designed to show only red blood cells may also show red blood cells that are touching white blood cells. The touching red blood cells may be digitally removed from images to make it easier for the computer to detect the white blood cell borders in order to make more accurate cellular measurements and enumeration. Light emitted at 570 nm may be useful to provide high contrast images for platelets and nuclei. Other wavelengths may be chosen in order to best discriminate the colors of basophils, monocytes, lymphocytes (all shades of blue), eosinophils (red), and neutrophils (neutral color). For counting platelets, for example, two colors of illumination may be used (such as 430 nm and 570 nm). A high contrast image may be obtained by subtracting the 430 nm image from the 570 nm image. Light having a wavelength of 430, 500, 525 or 600 is particularly effective at showing cell color information, although the light emission device may use light at wavelengths between 400 nm and 700 nm inclusive. These wavelengths will also be used for the display of the color images if appropriate. Otherwise one or two additional images may need to be taken for the 200+ cells that will be analyzed for the differential count and which may be shown on the display 320. Typically the narrow-band images will be chosen from the range of 400 nm to 750 nm. Test results have shown that two to eight separate light colors to work well, with three to four separate light colors being optimal. The computer 300 may be able to further refine the images by compensating for spatial shifts. Also the computer may combine the various colored images to generate multi color images for display or analysis. Numeric descriptors of the individual images or combined images can be used to determine spatial, densitometric, colorimetric and texture features of the cells for classification of the cell types. A further advantage of using narrow band illumination is that narrow band illumination allows for the elimination of the use of oil objectives or coverslips. Light is refracted when the light passes from glass to air. Prior art systems have used oil objectives or coverslips to minimize this refraction at air to glass transitions, but having to add oil or coverslips adds steps to processing the slides, and increases the per slide preparation time and analysis cost. To overcome this deficiency of the prior art systems, a combination of narrow band LEDS or filtered light can be used without the need to use coverslips or oil. Reducing the variance or bandwidth in the wavelengths of the light decreases the distortion in the image captured by the light receiving device 200 when the light passes through the slide 701. The computer 300 may also instruct the light emission device 600, to focus the light from the light source (either 610 or 630) so that the light is properly focuses on the slide. To do this, the computer 300 may instruct a focus adjustor to optimize the focus for each color of light.

The Slide Apparatus 700

Figure 2:
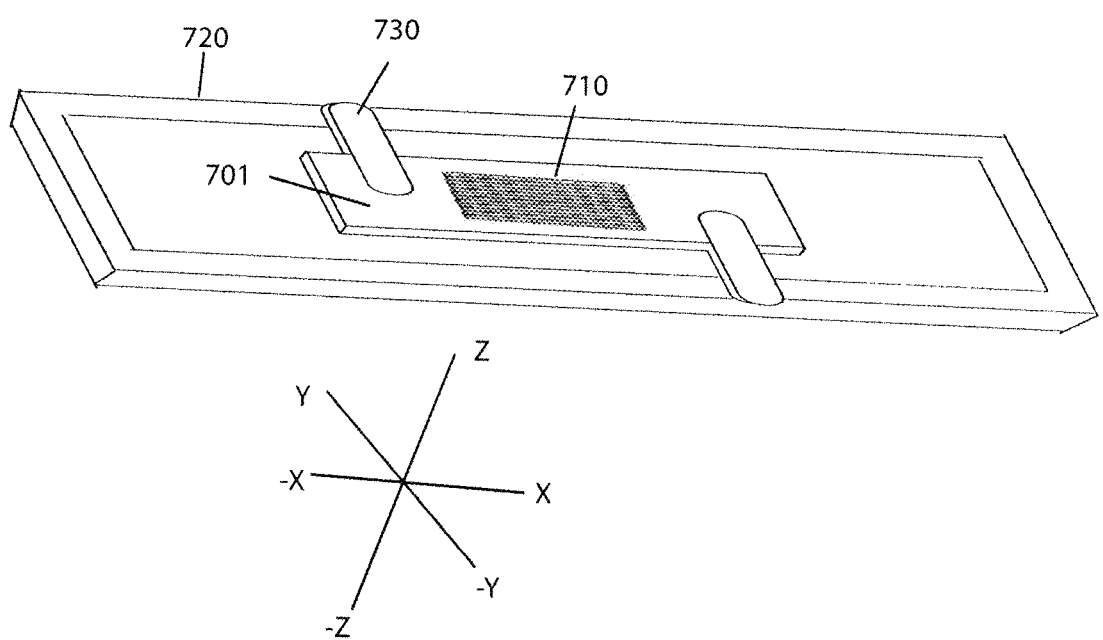
FIG. 2: is a perspective view of a slide and slide holder.

FIGS. 1A, 2, and 3 illustrate an embodiment of the slide apparatus 700 comprising a slide 701, a specimen zone 710, a slide frame 720, and a slide holder 730. However, other embodiments of the invention may not require the use of a slide holder 730 or slide frame 720. Additionally the specimen zone 710 boundary mark is optional as well, and may comprise one or more hydrophobic rings or other painted marks. These rings may help contain the blood sample, and also make reviewing images of the slides easier by quickly locating the specimen zone when a slide is viewed manually under a microscope (the may also assist the analysis process in interpreting the image.) The rings may also assist in facilitating the transfer of the stain onto the slides. Additionally, while the specimen zone has been illustrated as a rectangle other shapes such as a circle or triangle may be used. Different size specimen zones may be used, including zones having a total area of one half to three square centimeters. The slide 701 may be manufactured from glass or plastic and may be 1 inch tall by 3 inches wide by 1 mm thick. Also shown on FIGS. 2 and 3 is a fluid sample dispersed on the slide in flows 750. The fluid can be dispersed in flows as shown in FIG. 3, or in a spiral pattern as shown in FIG. 4.

The Discharge Device 900

Figure 1B:
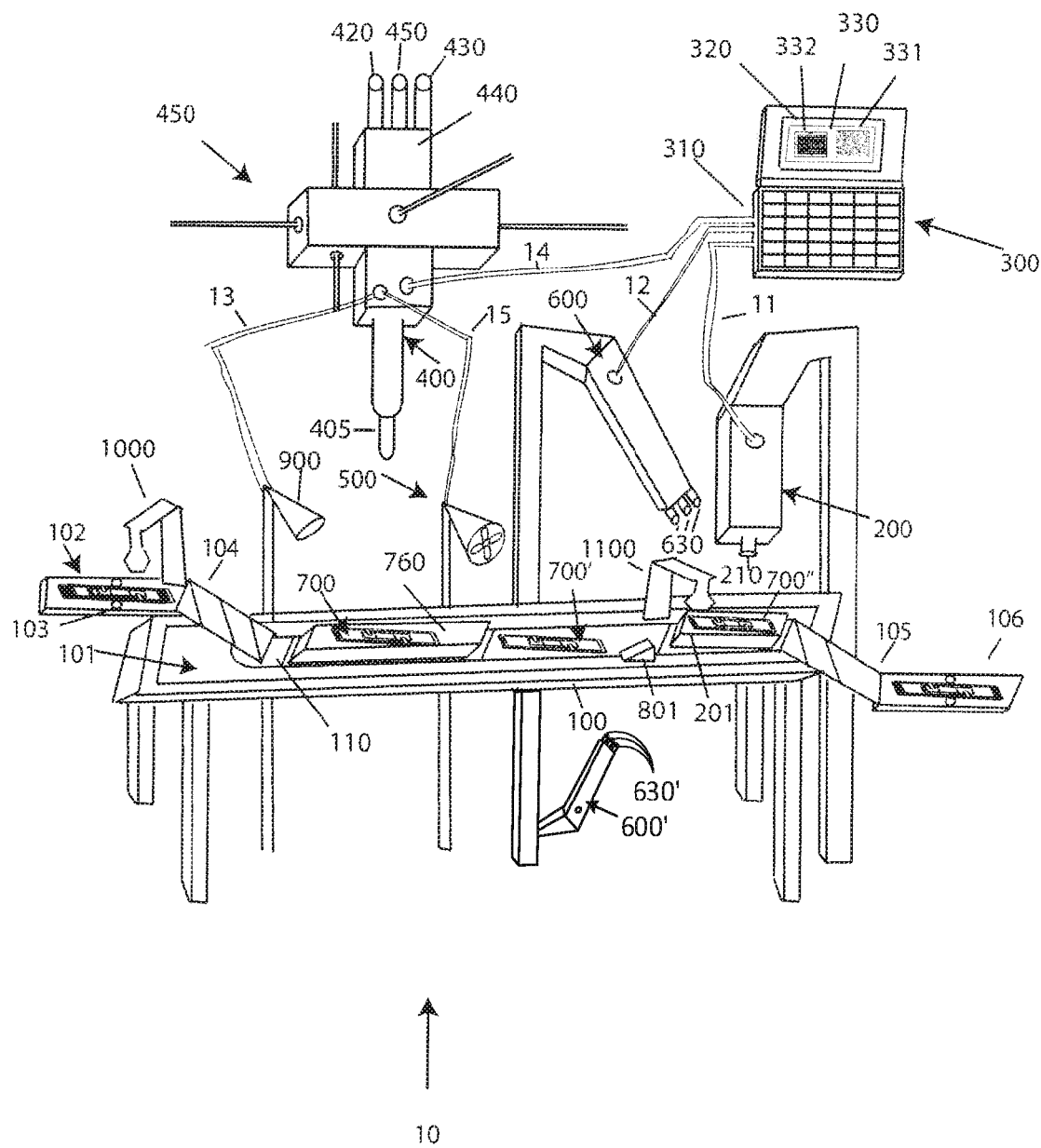
FIG. 1B: is a perspective, schematic view of a system for analyzing body fluids.

With reference to FIG. 1B, the system may comprises a discharge device 900 for pretreating the slide 701. The discharge device may take the form of a corona discharge device. The discharge device 900 may clean the slide 701 by creating a high intensity heat to burn off small particles to clean the slide to create a hydrophilic surface. Electro-Technic Products, Sawicki, Pa., makes a corona discharge device compatible with embodiments of the present invention. To perform the pretreatment, the computer 300 would turn on the discharge device 900, and cause the slide apparatus controller 760 to move the slide in a spiral or raster motion for about 15 seconds (though a range of 1-20 seconds could be used). The discharge device may be set at an angle from the slide, or may be positioned directly above the slide. Typically, the discharge device 900 may be positioned approximately 10 to 20 mm above the slide.

The Slide Labeler 1000 and Slide Label Reader 1100

The system 10 may optionally include a slide labeler 1000 and optionally a slide label reader 1100. The slide label reader 1000 may be situated on the platform 100 near the feeder 102 as shown in FIGS. 1A and 1B or may be free standing or attached to other components. Slide labeler 1000 may place a label on the slide. A label 770 may include items such as stickers, barcodes, RFID tags, EAS tags, or other type of markings on the slide. FIG. 3 shows an exemplary slide having a UPC bar code label on it, but other markings conventions may be used. Moreover, the markings may be applied directly to the slide via paint or ink, or may they may be stuck to the slide using a writing medium and an adhesive (for example, a sticker).

The system 10 may comprise a slide label reader 1100. Slide label reader 1100 may read markings placed on the slide from the slide labeler 1000 or by labelers external to the system. The slide label reader 1100 could comprise an interrogator, a bar code reader, or other optical device. In some embodiments, the system 10 may be able to determine information from the labels 770 without a slide label reader 1100 by using the light receiving device 200 to capture an image of the label 770. The computer 300 or the light receiving device (if it contains a processor and memory) could perform image processing on the image containing the label and determine the information about the label 770.

Bone Marrow

As discussed above, the present invention may be used to analyze peripheral or whole blood. The invention can also be used, however, to study cells of various types of fluids comprising bone marrow, urine, vaginal tissue, epithelial tissue, tumors, semen, spittle, and other body fluids For example, the preparation methods and analysis techniques described here can also be applied to bone marrow aspiration samples. Bone marrow samples have a higher cellular density and contain many immature red and white blood cell types that are seldom found in peripheral blood. The technique of preparing a thin layer of cells, staining with a Romanowsky stain and analyzing with image analysis can be applied to bone marrow aspirates as well, however more sophisticated image analysis may be needed to discriminate the additional types of cells.

As with peripheral blood samples, bone marrow samples may be collected into a container with an anticoagulant. This anticoagulant may be EDTA or heparin. Additional diluting or preserving fluid may be added to the sample. In the instrument described here a bone marrow sample would be prepared by first agitating the sample to provide a thorough mixing. Due to the uncertain cellular density of such samples one or more dilutions may be prepared and pipetted onto the slide or slides. In one embodiment, a triple dilution process may be used to create three specimens. A first specimen may be created by adding 2 parts diluent to one part bone marrow. The first specimen may then be dispensed onto a first portion of the specimen zone 710 of the slide 701. A second specimen may be created by adding four parts diluent to the bone marrow. The second specimen may then be dispensed onto a second portion of the specimen zone 710 of the slide 701. A third specimen may be created by adding eight parts of diluent to the marrow. The third may then be dispensed onto a third portion of the specimen zone 710 of the slide 701.

For viscous body fluids, including but not limited to bone marrow, it may be desirable to provide the system 10 with a serial dilution mechanism(?). In one embodiment of this process, the applicator 400 can direct one or more flows of cells onto a slide 701. The light receiving device 200 can capture an image of the flows of cells, and the computer 300 can determine whether the flows are sufficiently dilute for forming a monolayer of cells on the slide, performing an accurate count of a particular cell type, or capturing images that allow for an assessment of cellular morphology. If the flows are not sufficiently dilute, the computer can instruct the mixer 440 to further dilute the body fluid. The applicator 400 can then apply a more dilute flow of cells to the slide 701, which the light receiving device 200 can image. The computer 300 can again determine whether the flows are sufficiently dilute for forming a monolayer, counting, or assessining morphololgy and if not, the system 10 can instruct the mixer 440 to further dilute the body fluid. This process can be repeated until a sufficiently dilute body fluid sample is created. In some embodiments, the applicator 400 will apply flows of cells along the entire slide before the light receiving device 200 images the cells. In other embodiments, a subset of cells flows (e.g. 3-10) may be applied before the cells flows are imaged. In some embodiments, the computer 300 can analyze the captured image of the flow of cells, and determine an approximate amount of diluent necessary to dilute the body fluid so that subsequent flows of cells may be counted when they are imaged. In other embodiments, the system 10 may contain preset dilution intervals to as apply if the system determines the current dilution ratio is not sufficient (i.e. if the flows are not sufficiently dilute, try 1:1 (diluent:body fluid). If 1:1 is too low and the flows are still not sufficiently dilute, try 2:1 (diluent:body fluid), etc.) In some embodiments, a user of the system can select via a user input specific dilution intervals for the body fluid such as no diluent, 3:2 (dilutent:body fluid); 4:1; or 8:1. In some embodiments, the applicator 400 may place a first group of flows of cells onto a slide; a second group of flows of cells onto the slide; a third group of flows of cells onto the slide, etc; wherein each group of flows of cells has a different diluent to body fluid ratio. Alternatively, the applicator 400 may apply a first group of flows of cells onto a first slide; a second group of flows of cells onto a second slide; a third group of flows of cells onto a third slide, etc; wherein each group of flows of cells has a different diluent to body fluid ratio. Finally, while the above serial dilution process is contemplated to be especially useful for viscous body fluids such as bone marrow, this process may be used for less viscous body fluids such as peripheral blood or semen as well.

For the image analysis, a low magnification assessment of the cellular area on the slide could chose the optimum one third for subsequent analysis. Once the proper area of the slide is selected, 200+ bone marrow cells would be measured to determine the differential count.

Reticulocytes

The system 10 may also count the number of reticulocytes in a blood sample. Using a Romanowsky stain to mark RNA, the computer 300 can count the number of reticulocytes present in the specimen. When a Romanowsky stain is used, the reticulocytes appear slightly bluer than other red blood cells, and are usually slightly larger. The computer 300 can use its analysis process (16A or 17B, of FIGS. 7A and 7B) to quantify the blue component of the red cells. The analysis process could measure integrated optical density of a cell's difference image created by subtracting one image taken with blue light of 430 nm (range of 400 to 470 nm) from an image taken with non-blue light of 600 nm (range of 470 to 750 nm). The analysis process could correlate the number of red blood cells with a defined range of integrated blue component to a number of reticulocytes counted manually or by flow methods using special stains. The accuracy of the analysis process can be further improved by requiring the analysis process (16A or 17B) to measure the size, shape, color, and measured characteristics of cellular objects. For example, the analysis process could detect the difference between a red blood cell with a bluish platelet lying under or over a red blood cell as opposed to a true reticulocyte. In other embodiments, a special stain may be used to mark RNA in the cells, and an imaging method could be used to detect the presence of this stain.

Process Flows

Figure 7A:
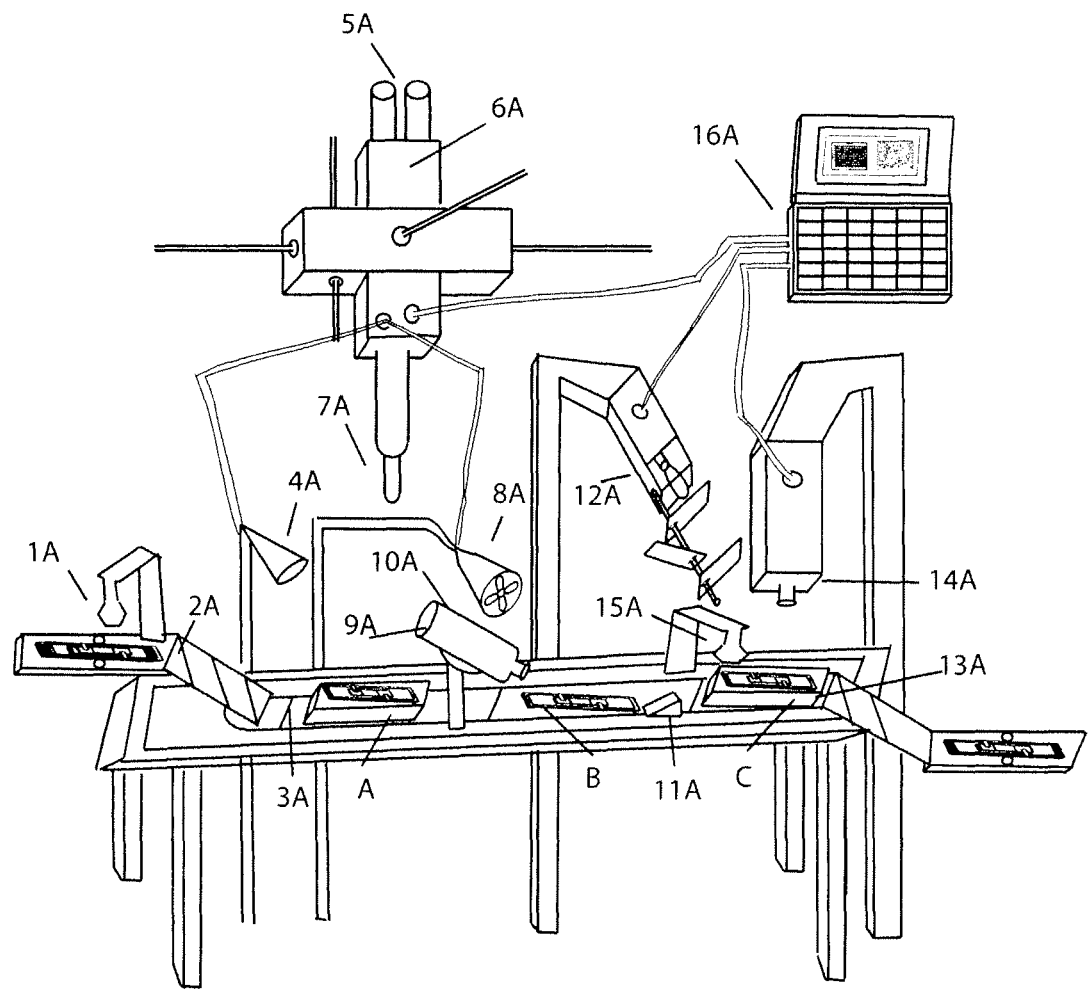
FIG. 7A: is a process flow schematic of the embodiment shown in FIG. 1A.
Figure 7B:
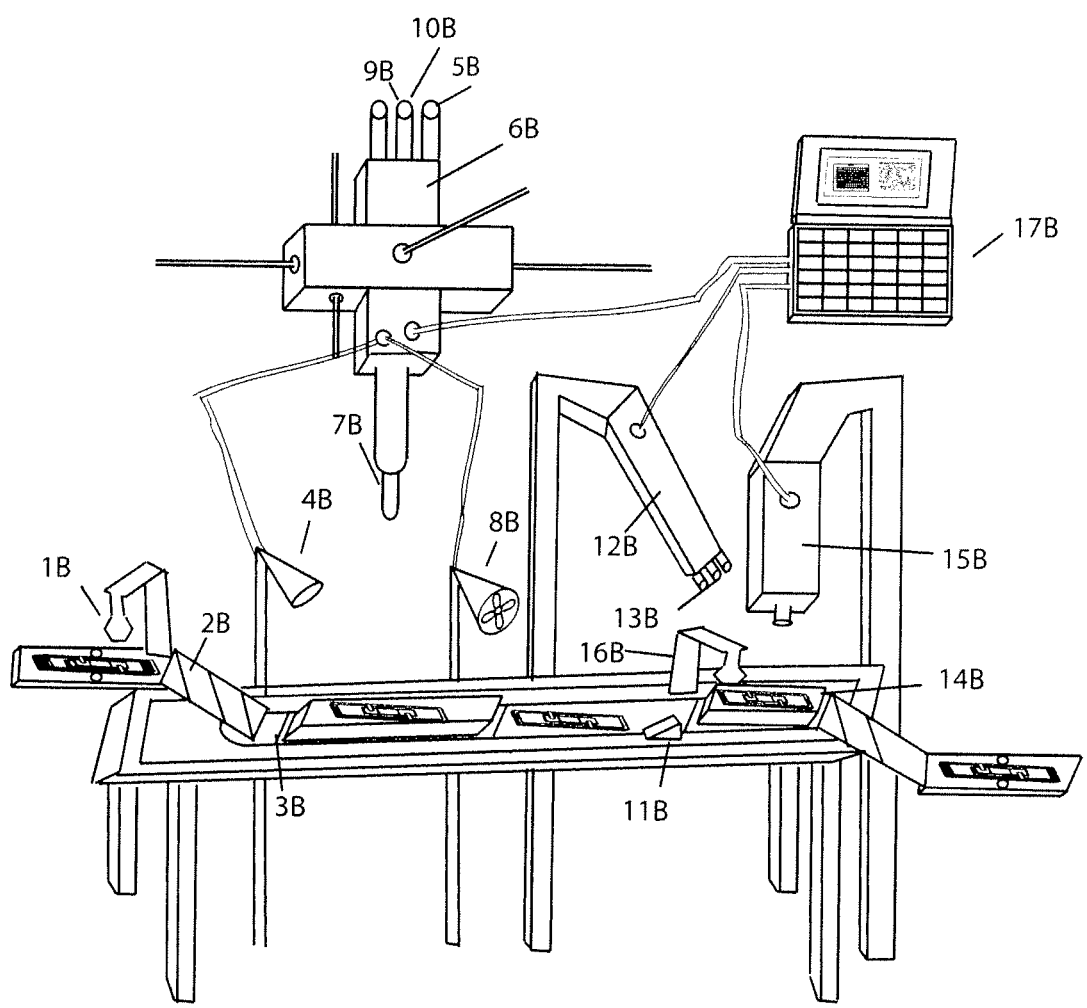
FIG. 7B: is a process flow schematic of the embodiment shown in FIG. 1B.

Embodiments of the present invention are contemplated to process multiple slide apparatuses 700 in a pipelined series as shown in FIG. 1A or 1B, but embodiments which process the slide apparatuses 700 in parallel may also be constructed. Embodiments may be constructed which can process a large number (e.g. 10-20) of slide apparatuses in series or in parallel, or smaller volume systems 10 can be constructed (processing 4-8 slides at a time.) The following two paragraphs describe an example process flow for FIGS. 1A and 1B, but alternate process flows are possible and feasible through alternate embodiments of the invention. These process flows are also illustrated in FIGS. 7A and 7B. Additionally, other configurations of the system are possible, and would likely have different process flows. Moreover, although the steps are presented in a series, many of the steps may be presented in a different order or performed simultaneously. Finally, most of the following steps are optional, and may be removed from the process flow.

In the embodiment shown in FIGS. 1A and 7A, the software stored in the memory of the computer 300 may cause the computer to control the order, speed, and variables associated with processes 1A-16A. The process may begin with computer 300 sending an instruction to the slide labeler 1000 to place a label 770 on the slide 701. The labeling process 1A, may be performed in the feeder 102 or may be performed on the ramp 104 or at the slide apparatus controller 760. To move the slide apparatus 700 from the feeder 102, the computer 300 may send an instruction to the feeder 102 to activate the feeder propulsion mechanism 103. The computer 300 may also cause a feeder process 2A to begin which may include moving the slide apparatus 700 onto the advancer 110. The feeder process may include utilizing the sensor to determine how many slides are in the feeder 102. The computer may cause the advancer 110 to initiate an advancing process 3A including moving the slide to the application station A, and onto the slide apparatus controller 760 (if one is present). Once the slide apparatus is on the slide apparatus controller, the slide may be pretreated by the discharge device 900. The pretreatment process 4A may include the slide controller 760 rotating or spinning the slide apparatus 700 as the discharge device burns the debris from the slide 701. Once the optional pretreatment process 4A is completed the applicator process 5A may begin. The applicator process 5A may comprise having an operator fill the reservoir tank 420 with diluent and reservoir tank 430 with body fluid. Body fluids such as urine, vaginal tissue, epithelial tissue, tumors, semen, spittle, peripheral blood, bone marrow aspirate or other body fluids may be used. Alternatively, the fluids may be aspirated automatically from a patient's sample vial. The mixer 440 may begin the mixing process 6A to mix the diluent with the body fluid in a certain ratio such as 2:1 (body fluid:diluent) to form a diluted body fluid. To apply the diluted body fluid to the slide 701, one of two body fluid application processes 7A or 7B (FIGS. 7A and 7B, described above in conjunction with the applicator 400) may be performed (but either process could be used for both embodiments). After the application completes, the advancer 110 may continue the advancing process moving the slide apparatus to a second station B. Once the body fluid application process 7A is completed, the drying process 8A may begin. The drying process may include using the gas movement device 500 to direct gas onto the slide for a period of time (such as 20-30 seconds). Once the slide is dried, the body fluid may be fixed using the fixation process 9A. After the body fluid is fixed, it may be stained using the staining process 7A. After the body fluid is stained, the excess stain may be removed using a stain removing process 11A. The stain removing process 11A may include a slide tilting process wherein the slide is tilted at least partially in order to allow the stain and or fixative to drain off the slide. To capture images of the specimen, the advancer 110 may continue advancing the slide apparatus to the imaging station C. At the imaging station C, the system may activate specimen illuminating process 12A and an imaging process 15A, which uses the light emission device 600 and light receiving device 200 respectively to illuminate the specimen and to capture images of the illuminated specimen. The computer 300 may direct the light emission device to apply to different filters to the light to change the wavelength of emitted light using the light filtration process 13A. Alternatively, the LED illumination process of 13B may emit one or more wavelengths of light if a light emission device 600 comprises one or more LEDs. A slide movement process 14A may be performed by the slide mover 201 to position the slide 701 in various X, Y, Z directional positions. Since in many embodiments, the magnification of the lens of the light receiving device will generate a view field that only contains a part of the total area of the specimen, the slide movement process 14A may be utilized to move the specimen into different X, Y positions allowing the light receiving device 200 to take multiple images 331 to capture the entire specimen. The slide mover may also be able to move the slide to multiple imaging stations allow light receiving devices to take images at various magnifications. The slide mover may also be able to move the slide in the Z direction allowing one or more light receiving devices to take images at various magnifications, focus position and light wavelengths. The system 10 may use the label reader 1100 to read the labels on the slides (using the label reading process 15A), or alternatively the computer may recognize symbols on the label using image recognition software. The light receiving device may transfer the images to the computer through link 11. The computer may save the images in internal memory and use its software to analyze the images (using the analysis process 16A) to count the cells and perform calculations on the resulting data. The software may generate results including tables, charts, or a graph of the results 332, and may display the images 331 on the display 320 of the computer 300.

A second process flow is shown in FIG. 7B (also refer to FIG. 1B). The process may begin with computer 300 sending an instruction to the slide labeler 1000 to place a label 770 on the slide 701. The labeling process 1B, may be performed in the feeder 102 or may be performed on the ramp 104 or at the slide apparatus controller 760. To move the slide apparatus 700 from the feeder 102, the computer 300 may send an instruction to the feeder 102 to activate the feeder propulsion mechanism 103. The computer 300 may also cause a feeder process 2B to begin which may include moving the slide apparatus 700 down the ramp 104 onto the advancer 110. The feeder process 2B may include utilizing the sensor to determine how many slides are in the feeder 102. The computer may cause the advancer 110 to initiate an advancing process 3B including moving the slide to the application station A, and onto the slide apparatus controller 760 (if one is present). Once the slide apparatus is on the slide apparatus controller 760, the slide 701 may be pretreated by the discharge device 900. The pretreatment process 4B may include the slide controller 760 rotating or spinning the slide apparatus 700 as the discharge device burns off any debris on the slide 701. Once the optional pretreatment process 4B is completed the applicator process 5B may begin. The applicator process 5B may comprise having an operator fill the reservoir tank 420 with diluent and reservoir tank 430 with body fluid. Alternatively, the fluids may be aspirated automatically from a patient's sample vial. Body fluids such as peripheral blood or bone marrow aspirate may be used, although fluids comprising bone marrow, urine, vaginal tissue, epithelial tissue, tumors, semen, spittle, and other body fluids may be prepred and analyzed using embodiments of the invention. The applicator 400 may contain a third reservoir for containing the stain, and perhaps a fourth reservoir for containing fixative (however, in other embodiments the stain and fixative could be stored in the same reservoir). The mixer 440 may begin the mixing process 6B to mix the diluent with the body fluid (and possibly the stain and fixative) in a certain ratio such as 2:1 (body fluid:diluent) to form a diluted body fluid. In these embodiments, the applicator 400 would apply the stain and or the fixative after the body fluid is applied to the slide using the staining process and fixative process respectively. Once the slide is dried, the body fluid may be fixed using the fixation process 9B. After the body fluid is fixed, it may be stained using the staining process 7B. To apply the diluted body fluid to the slide 701, one of two body fluid application processes 7A or 7B (described above in conjunction with the applicator 400) may be performed (but either process could be used for both embodiments). Once the body fluid application process 7B is completed, the drying process 8B may begin. The drying process may include using the gas movement device 500 to direct gas onto the slide for a period of time (such as 20-30 seconds). After the body fluid is stained and fixed, the stain may be removing using a stain removing process 11B. The stain removing process 11B may include a slide tilting process wherein the slide is tilted at least partially in order to allow the stain and or fixative to drain off the slide. To capture images of the specimen, the advancer 110 may continue advancing the slide apparatus to the imaging station C. At the imaging station C, the system may activate specimen illuminating process 12B and an imaging process 15B, which uses the light emission device 600 and light receiving device 200 respectively to illuminate the specimen and to capture images of the illuminated specimen. The computer 300 may direct the light source 600 to apply a sequence of narrow band light onto the slide 701 using LED illumination process 13B. Alternatively, if a light emission device 600 with filters is provided, the computer 300 may direct the light emission device to radiate light and apply different filters to the light to change wavelength of emitted light using a light filtration process 13A. Once slides are illuminated, a slide movement process 14B may be performed by the slide mover 201 to position the slide 701 in various X, Y, Z positions. Since in many embodiments, the magnification of the lens of the light receiving device will generate a view field which only contains a part of the total area of the specimen, the slide movement process 14B may be utilized to move the specimen into different X, Y positions allowing the light receiving device 200 to take multiple images to capture the entire specimen. The slide mover may also be able to move the slide to multiple imaging stations that allow light receiving devices to take images at various magnifications. The slide mover may also be able to move the slide in the Z direction to allow the light receiving device to take images at various magnifications. The system 10 may use the label reader 1100 to read the labels on the slides (using the label reading process 16B), or alternatively the computer may recognize symbols on the label using image recognition software. The light receiving device may transfer the images to the computer through link 11. The computer may save the images in internal memory and use its software to analyze the images (using the analysis process 17B) to count the cells and perform calculations on the resulting data. The software may generate results including tables, charts, or graph of the results, and may display the images 331 or the results 332 on the display 320 of the computer 300.

Test Results

To determine the accuracy of this method, computer algorithms were developed to count RBCs and WBCs from digital images taken from a fluid sample comprising blood.

Table 1 below shows a summary of data for 34 slides. "Invention" data represents red and white blood cell counts from slides produced using the method described above, and analyzed using image analysis counting algorithms. "Sysmex" data represents red and white blood cell counts from a commercial "flow-based" automated CBC analyzer. Note that the specimens include very high and very low red blood cell counts and white blood cell counts, respectively.

TABLE 1

| Specimen | Invention Count RBC × $10^6$ | Sysmex Count RBC × $10^6$ | Invention Count WBC × $10^3$ | Sysmex Count WBC × $10^3$ |
|---|---|---|---|---|
| 1 | 4.97 | 5.69 | 5.00 | 5.64 |
| 2 | 3.66 | 4.22 | 5.92 | 6.99 |
| 3 | 4.32 | 4.83 | 4.13 | 4.00 |
| 4 | 4.00 | 4.01 | 3.36 | 2.91 |
| 5 | 4.27 | 4.22 | 9.66 | 8.48 |
| 6 | 2.83 | 3.20 | 8.60 | 9.25 |
| 7 | 4.46 | 4.79 | 5.80 | 6.40 |
| 8 | 4.04 | 4.78 | 4.02 | 4.63 |
| 9 | 2.98 | 3.10 | 10.02 | 10.16 |
| 10 | 4.88 | 5.04 | 6.24 | 6.44 |
| 11 | 2.95 | 3.29 | 7.28 | 8.43 |
| 12 | 4.47 | 4.97 | 6.75 | 7.70 |
| 13 | 2.75 | 3.01 | 4.91 | 4.62 |
| 14 | 4.35 | 4.73 | 8.48 | 9.27 |
| 15 | 3.82 | 4.16 | 6.26 | 6.06 |
| 16 | 3.16 | 3.50 | 14.49 | 14.97 |
| 17 | 3.87 | 4.22 | 5.37 | 4.67 |
| 18 | 3.69 | 4.04 | 3.75 | 3.50 |
| 19 | 4.08 | 4.51 | 11.42 | 11.22 |
| 20 | 3.03 | 3.26 | 2.00 | 1.87 |
| 21 | 3.23 | 3.49 | 6.68 | 6.50 |
| 22 | 4.35 | 4.63 | 10.09 | 9.95 |
| 23 | 2.84 | 3.03 | 10.28 | 11.62 |
| 24 | 3.02 | 3.27 | 0.59 | 0.57 |
| 25 | 2.75 | 2.87 | 17.06 | 16.42 |
| 26 | 2.78 | 3.01 | 5.80 | 5.56 |
| 27 | 2.73 | 2.90 | 8.84 | 8.28 |
| 28 | 2.97 | 2.98 | 17.18 | 17.41 |
| 29 | 3.56 | 3.75 | 16.70 | 16.79 |
| 30 | 2.91 | 3.16 | 7.05 | 7.89 |
| 31 | 3.32 | 3.55 | 9.80 | 9.73 |
| 32 | 3.01 | 3.29 | 45.00 | 44.62 |
| 33 | 4.77 | 5.24 | 6.11 | 6.44 |
| 34 | 4.34 | 4.57 | 7.01 | 6.89 |

Table 1 shows the raw data from counts performed on 34 vials. The second and third columns shows the red blood cell counts expressed as millions per microliter of patient blood for the invention count and the Sysmex count, respectively. The fourth and fifth columns shows the white blood cell counts expressed as thousands per microliter of patient blood for the invention count and the Sysmex count, respectively.

TABLE 2

| Vial | SysmexRBCs | RBCcounts | RBCscaled | SysmexWBCs | WBCcounts | WBCscaled |
|---|---|---|---|---|---|---|
| 1 | 5.69 | 1241765 | 4.97 | 5.64 | 1250 | 5.00 |
| 2 | 4.22 | 915262 | 3.66 | 6.99 | 1481 | 5.92 |
| 3 | 4.83 | 1080856 | 4.32 | 4.00 | 1033 | 4.13 |
| 4 | 4.01 | 998828 | 4.00 | 2.91 | 840 | 3.36 |
| 5 | 4.22 | 1068411 | 4.27 | 8.48 | 2414 | 9.66 |
| 6 | 3.20 | 707250 | 2.83 | 9.25 | 2149 | 8.60 |
| 7 | 4.79 | 1115913 | 4.46 | 6.40 | 1451 | 5.80 |
| 8 | 4.78 | 1010933 | 4.04 | 4.63 | 1006 | 4.02 |

TABLE 2-continued

| Vial | SysmexRBCs | RBCcounts | RBCscaled | SysmexWBCs | WBCcounts | WBCscaled |
|---|---|---|---|---|---|---|
| 9 | 3.10 | 744241 | 2.98 | 10.16 | 2504 | 10.02 |
| 10 | 5.04 | 1220400 | 4.88 | 6.44 | 1559 | 6.24 |
| 11 | 3.29 | 736701 | 2.95 | 8.43 | 1819 | 7.28 |
| 12 | 4.97 | 1117506 | 4.47 | 7.70 | 1688 | 6.75 |
| 13 | 3.01 | 687645 | 2.75 | 4.62 | 1228 | 4.91 |
| 14 | 4.73 | 1086737 | 4.35 | 9.27 | 2120 | 8.48 |
| 15 | 4.16 | 955279 | 3.82 | 6.06 | 1564 | 6.26 |
| 16 | 3.50 | 789218 | 3.16 | 14.97 | 3622 | 14.49 |
| 17 | 4.22 | 967780 | 3.87 | 4.67 | 1343 | 5.37 |
| 18 | 4.04 | 922880 | 3.69 | 3.50 | 937 | 3.75 |
| 19 | 4.51 | 1019878 | 4.08 | 11.22 | 2855 | 11.42 |
| 20 | 3.26 | 757606 | 3.03 | 1.87 | 500 | 2.00 |
| 21 | 3.49 | 808679 | 3.23 | 6.50 | 1670 | 6.68 |
| 22 | 4.63 | 1086451 | 4.35 | 9.95 | 2522 | 10.09 |
| 23 | 3.03 | 709164 | 2.84 | 11.62 | 2571 | 10.28 |
| 24 | 3.27 | 753952 | 3.02 | 0.57 | 147 | 0.59 |
| 25 | 2.87 | 688731 | 2.75 | 16.42 | 4265 | 17.06 |
| 26 | 3.01 | 695059 | 2.78 | 5.56 | 1451 | 5.80 |
| 27 | 2.90 | 682449 | 2.73 | 8.28 | 2209 | 8.84 |
| 28 | 2.98 | 741274 | 2.97 | 17.41 | 4295 | 17.18 |
| 29 | 3.75 | 890278 | 3.56 | 16.79 | 4174 | 16.70 |
| 30 | 3.16 | 727660 | 2.91 | 7.89 | 1762 | 7.05 |
| 31 | 3.55 | 831027 | 3.32 | 9.73 | 2450 | 9.80 |
| 32 | 3.29 | 753365 | 3.01 | 44.62 | 11250 | 45.00 |
| 33 | 5.24 | 1193348 | 4.77 | 6.44 | 1527 | 6.11 |
| 34 | 4.57 | 1085941 | 4.34 | 6.89 | 1753 | 7.01 |
| | RBC Correlation ($R^2$) | | 97.95% | WBC Correlation ($R^2$) | | 99.70% |

Table 2. Table 2 shows the raw data from counts performed on 34 vials. The $2^{nd}$ column gives the reference (Sysmex) RBC counts, while the $3^{rd}$ column reports the automated counts from the microscope slide. The $4^{th}$ column scales the counts to million cells per microliter, assuming a 1:4 dilution. The $5^{th}$-$7^{th}$ column show the data for the WBC counts. At the bottom of the table are the calculated correlation coefficients (R-squared).

The data was obtained from 34 patient samples during two sessions of preparing slides. The data is representative of typical patients, although the tubes were selected from patients with a wide distribution of red and white cell counts. Most, if not all of the 34 samples, were obtained from specimens "archived" during the day in the refrigerator, and then pulled and prepared on the instrument in the late afternoon. Once the tubes were pulled, they were processed consecutively.

The algorithms were first validated by comparing manually counted microscope fields to the automated counts. There is a high correlation between the manually counted cells and the automatically counted cells.

Figure 5:
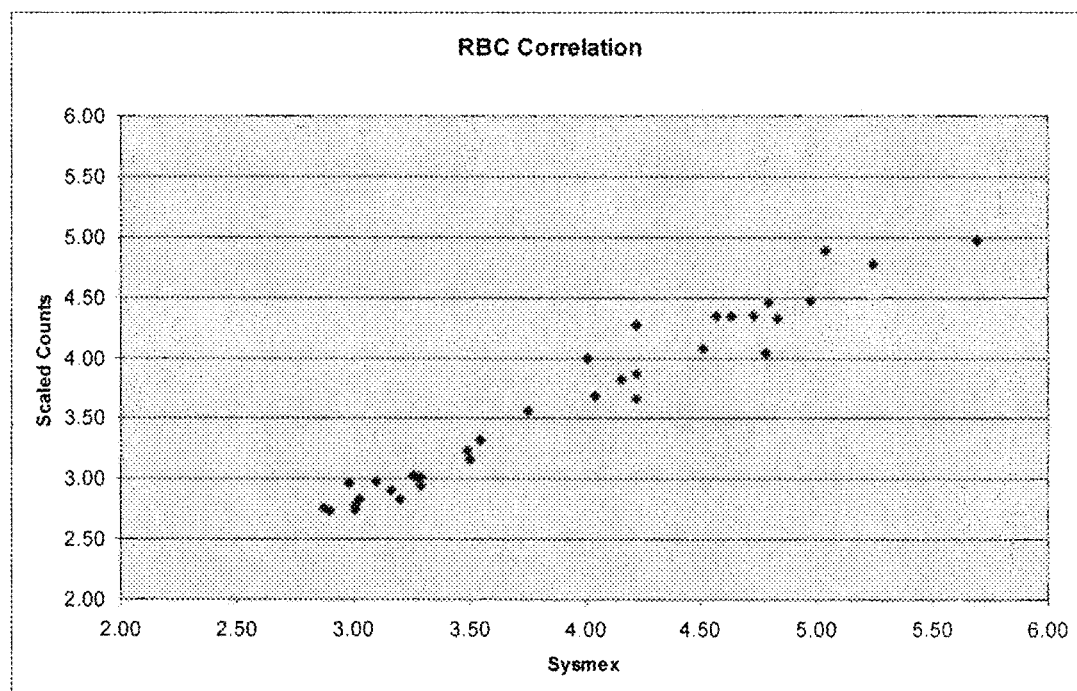
FIG. 5: is a graph illustrating the correlation between SYSMEX® brand hematology analyzer (hereinafter "Sysmex") RBC counts and the RBC counts generated using an embodiment of the invention.
Figure 6:
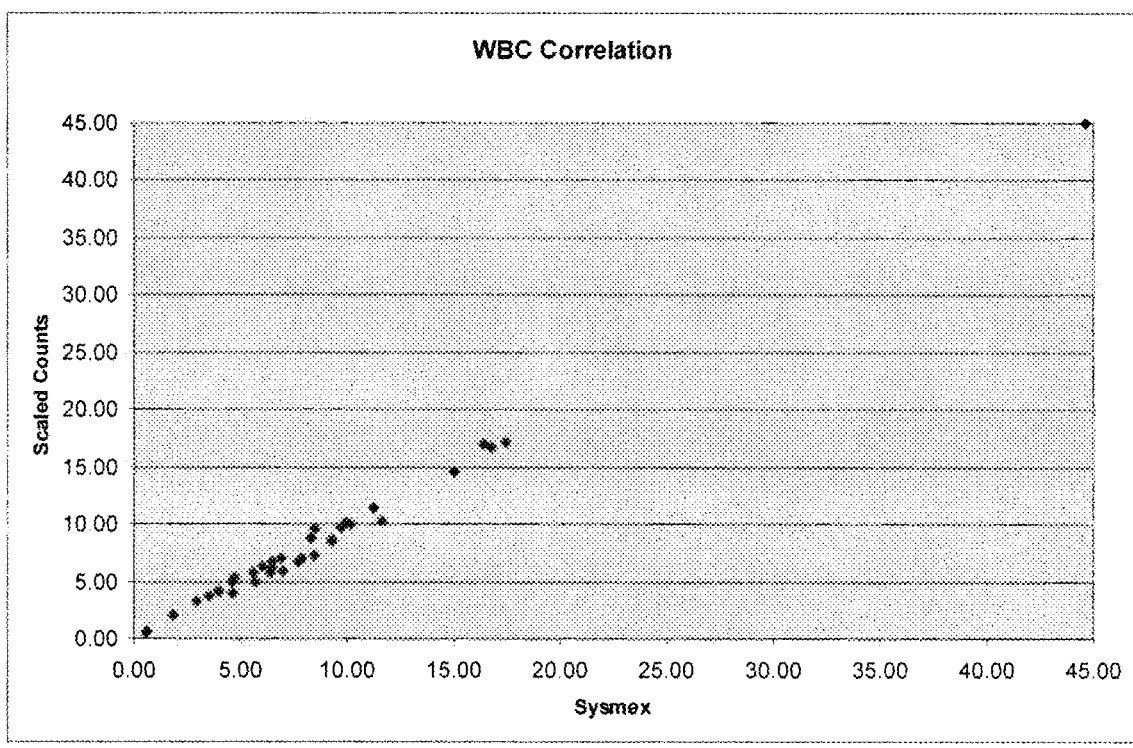
FIG. 6: is a graph illustrating the correlation between Sysmex WBC counts and the WBC counts generated using an embodiment of the invention.

High correlation between the two methods was found for both the red blood cell counts and the white blood cells counts (see Tables 1 and 2 and FIGS. 5 and 6). The graph of FIG. 5 shows the correlation between the Sysmex counts and the automated slide based counts for the red blood cells. The data points are tightly clustered and form a line that indicates that the numbers on the vertical axis (the invention counts) are similar to the numbers on the horizontal axis (the Sysmex counts). Typically for such data a correlation coefficient (R-squared) can be calculated to show the degree of agreement, where 100% would be perfect agreement. An R-squared value of 97.95% was calculated for this red blood cell data, indicating a high degree of agreement and similar to what two different automated instruments might show. The graph shown in FIG. 6 shows the correlation between the Sysmex counts and the automated slide counts for the white blood cells. The raw counts varied between 147 and 11,250 white blood cells per slide. An R-squared value of 99.70% was calculated for this white blood cell data, indicating a high degree of agreement and similar to what two different automated instruments might show. This confirms that the novel approach to quantitative transfer of cells was successful and that automated cell counts from computer imaging yielded accurate results.

Exemplary Process for CBC and White Blood Cell (WBC) Differential

The following sequence of steps may be performed in any order and some steps may be omitted or replaced with other steps.

Step 1. Extract a known volume of blood from a tube filled with a patient's blood.

Step 2. Dilute the blood if necessary. For example, one may use 5% albumin in distilled water as a diluent.

Step 3. Spread a known volume of blood or blood plus diluent over an area on a glass microscope slide in a thin layer. The slide may be treated to produce a hydrophilic surface to spread the cells better. The slide may be treated to allow optimal adherence of the blood elements to the slide.

Step 4. Allow the slide to dry in the air, or assist the drying using light air or heat.

Step 5. Capture an image without a coverslip using a "dry" objective that is corrected for no coverslip, for example one may use a 10× or 20× objective coupled to a CCD camera. Determine the count in each image frame including Red Blood Cells (RBCs), and possibly White Blood Cells (WBCs), and platelets. One or more colors may be used, for example using a color camera or using narrow band illumination produced by an interference filter or LED. Measurement of hemoglobin content may be done at this time as well.

Step 6. Fix and stain the cells on the slide. Fixation may be a separate step or combined with staining.

Step 7. Capture an image of stained slide without coverslipping, using a "dry" objective, to count RBCs, WBCs, and platelets and hemoglobin. This step may be in place of or in conjunction with step 5.

Step 8. Perform WBC differential count from high resolution images acquired without a coverslip, using a "dry" objective, for example with a 40× or 50× objective that is not corrected for a coverslip. A color camera or multiple black & white images taken using color filters or using LED illumination may be used. This step may be in addition to, or combined with Step 7.

Step 9. Calculate desired parameters and derived parameters required for the CBC.

Step 10. Display all CBC parameters to an operator in a Graphical User Interface (GUI).

Step 11. Display results of WBC differential to an operator in the GUI.

Step 12. Display images of RBCs, WBCs, platelets and any unusual/abnormal blood elements to an operator.

Step 13. Allow an operator to interact with the images and the parameters to "sign off" the CBC, WBC differential count, and identification of unusual or abnormal objects.

Step 14. If needed, update results of CBC and WBC counts depending on operator interaction in Step 13.

Step 15. Optionally, allow objects of interest to be relocated on a microscope that has a motorized, computer controllable stage to allow automated relocation of the objects for viewing.

Step 16. Optionally, update the results of the CBC and WBC counts depending on the microscopic operator interaction.

Although the exemplary process described above describes steps for preparing and examining a sample of blood, embodiments of the invention may be used to prepare and examine other fluids comprising bone marrow, urine, vaginal tissue, epithelial tissue, tumors, semen, spittle, and other body fluids.

It is claimed:

1. A system configured for analyzing red blood cells and white blood cells from a sample of a body fluid containing blood cells, the system comprising:
   a. a feeder for storing new transparent substrates;
   b. an application station comprising a mixer, a body fluid reservoir, a diluent reservoir, and an applicator tip for dispensing the body fluid containing a homogenous and quantifiable number of blood cells onto a transparent substrate, wherein the mixer, the body fluid reservoir, and the diluent reservoir are fluidly connected, and wherein the applicator tip is fluidly connected to the mixer and is arranged above the substrate;
   c. a preparation station comprising a dispenser for dispensing fixative and stain onto the cells on the transparent substrate;
   d. an imaging station comprising:
      i. a light source arranged on one side of the transparent substrate and configured to direct light through the transparent substrate to illuminate the blood cells on the transparent substrate; and
      ii. a light receiving device arranged on a side of the transparent substrate opposite the light source and configured to capture at least one image of the blood cells corresponding to light in a first wavelength range of 400 to 470 nm transmitted through the cells without capturing a fluorescent emission or light reflected off the transparent substrate, and at least one image of the cells corresponding to light in a second wavelength range of 470 to 750 nm transmitted through the cells without capturing a fluorescent emission or light reflected off the transparent substrate;
   e. an advancer for moving the transparent substrate through the system in order from the feeder, to the application station, to the preparation station, and to the imaging station;
   f. a display comprising a graphical user interface ("GUI") arranged to display images of cells:
   g. a computer comprising a microprocessor; and
   h. software instructions stored on a storage device for controlling the system, wherein when the microprocessor executes the software instructions the computer causes the system to:
      i. fill the applicator tip with a volume of the body fluid;
      ii. position the applicator tip above the transparent substrate;
      iii. dispense a known volume of body fluid including a quantifiable number of blood cells out of the applicator tip and while ejection of the body fluid onto the transparent substrate is occurring, maintaining relative movement between the tip and the transparent substrate to lay down the entire known volume of body fluid in two or more rows over a defined area of the transparent substrate, wherein the applicator tip height above the transparent substrate, a flow rate of the body fluid out of the applicator tip, and a speed of the relative movement are controlled such that blood cells in the body fluid settle onto the transparent substrate in a layer that is about one cell thick and such that morphology of the blood cells is sufficiently preserved to enable image-based cell analysis;
      iv. fix and stain the cells on the transparent substrate;
      v. control the light source to illuminate the cells on the transparent substrate;
      vi. activate the light receiving device to capture at least one image of the red blood cells ("RBCs") and at least one image of the white blood cells ("WBCs") corresponding to light in the first wavelength range transmitted through the cells without capturing a fluorescent emission or light reflected off the transparent substrate, and at least one image of the red blood cells and at least one image of the white blood cells corresponding to light in the second wavelength range transmitted through the cells without capturing a fluorescent emission or light reflected off the transparent substrate;
      vii. store the images in a memory;
      viii. automatically analyze the images of the RBCs and WBCs to determine whether the body fluid sample dispensed onto the substrate is sufficiently dilute or concentrated to form the about one cell thick layer of blood cells for analysis, wherein if the analysis of the images indicates that the body fluid sample on the substrate is too concentrated, the system adds more diluent from the diluent reservoir to the mixer to further dilute the body fluid, and if the analysis of the images indicates that the body fluid sample on the substrate is too dilute, the system adds more body fluid or concentrated body fluid from the body fluid reservoir to the mixer to further increase the body fluid concentration on the substrate;
      ix. automatically analyze the images of the RBCs and WBCs to determine a RBC count per microliter of the sample of body fluid and a WBC differential for the sample including a count of each type of WBC per microliter of the sample of body fluid; and
      x. display color images of a plurality of the RBCs and of a plurality of the WBCs based on the images captured by the light receiving device, the results of the RBC count, and the results of the WBC differential and the WBC counts in the GUI of the display, wherein the GUI is configured to allow an operator to interact with the color images and sign off on the RBC count results and the WBC differential results.

2. The system of claim 1, wherein the GUI is further configured to allow the operator to update the RBC results and WBC differential results.

3. The system of claim 1, wherein the software causes the system to display images of any unusual or abnormal blood elements.

4. The system of claim 1, wherein the images of the red blood cells displayed in the GUI include images of reticulocytes and a reticulocyte count.

5. The system of claim 1, wherein the body fluid is undiluted blood.

6. The system of claim 1, wherein the two or more rows form a contiguous monolayer of cells on a portion of the transparent substrate.

7. The system of claim 1, wherein the entire known volume of body fluid is dispensed onto the transparent substrate in four or more rows.

8. The system of claim 1, wherein the preparation station further comprises a substrate tilter for tipping the substrates to remove excess stain and fixative.

9. The system of claim 1, wherein the software causes the system to
   a. position the applicator tip less than about 110 microns above the transparent substrate;
   b. dispense the body fluid from the applicator tip at a rate of about 0.04 to 0.1 microliters per second; and
   c. maintain a speed of relative movement between the tip and the transparent substrate of about 10 to 100 millimeters per second.

10. The system of claim 1, wherein the application station further comprises a gas movement device configured to expose the substrate to a stream of flowing gas.

11. The system of claim 10, wherein the computer causes the system to control a rate of gas flow to which the substrate is exposed to adjust a drying time of the cells on the transparent substrate.

12. The system of claim 1, wherein the light receiving device is configured to capture images of the cells without the use of an immersion fluid.

13. The system of claim 1, wherein the light receiving device is configured to capture images of the cells when no cover slip is positioned atop the cells on the transparent substrate.

14. The system of claim 1, wherein the software causes the system to:
   a. direct the light source to generate light, and use a first filter to filter the generated light to produce first illumination light;
   b. illuminate the transparent substrate with the first illumination light, and capture the at least one image of the cells corresponding to light in the first wavelength range;
   c. direct the light source to generate additional light, and use a second filter to filter the additional light to produce second illumination light; and
   d. illuminate the transparent substrate with the second illumination light, and capture the at least one image of the cells corresponding to light in the second wavelength range.

15. The system of claim 14, wherein the software further causes the system to:
   a. direct the light source to generate additional light, and use a third filter to filter the additional light to produce third illumination light; and
   b. illuminate the transparent substrate with the third illumination light, and capture at least one image of the cells corresponding to light in a third wavelength range.

16. The system of claim 14, wherein the first wavelength range is between about 405 nm and 430 nm, and the second wavelength range is centered about 570 nm.

17. The system of claim 15, wherein the third wavelength range is selected from the range of 400 nm to 700 nm.

18. The system of claim 14, wherein the software causes the system to:
   a. refine the images by sharpening or compensating for spatial shifts or other distortions; and
   b. combine two or more images of the cells to generate a multi-color image, wherein the combined images comprise at least one image corresponding to the first illumination light, and at least one image corresponding to the second illumination light.

19. The system of claim 1, wherein the software causes the system to determine spatial, densitometric, colorimetric and texture features of the cells from the images for classification of a cell type.

20. The system of claim 1, wherein the light source comprises multiple light emitting diodes (LEDs), and wherein the software causes the system to:
   a. activate a first LED in the light source to generate first illumination light;
   b. illuminate the transparent substrate with the first illumination light, and use the light receiving device to capture the at least one image of the cells corresponding to light in the first wavelength range;
   c. activate a second LED in the light source to generate second illumination light; and
   d. illuminate the transparent substrate with the second illumination light, and use the light receiving device to capture the at least one image of the cells corresponding to light in the second wavelength range.

21. The system of claim 20, wherein the software further causes the system to:
   a. activate a third LED in the light source to generate third illumination light; and
   b. illuminate the transparent substrate with the third illumination light, and capture at least one image of the cells corresponding to light in a third wavelength range.

22. The system of claim 20, wherein the first wavelength range is between about 405 nm and 430 nm, and the second wavelength range is centered about 570 nm.

23. The system of claim 21, wherein the third wavelength range is selected from the range of 400 nm to 700 nm.

24. The system of claim 20, wherein the software causes the system to:
   a. refine the images by sharpening or compensating for spatial shifts or other distortions; and
   b. combine two or more images of the cells to generate a multi-color image, wherein the combined images comprise at least one image corresponding to the first illumination light, and at least one image corresponding to the second illumination light.

25. The system of claim 1, wherein the light receiving device is a CCD camera and the CCD camera captures black and white images.

26. The system of claim 1, wherein the system is configured to analyze a body fluid comprising urine, semen, spittle, peripheral blood, bone marrow aspirate, vaginal tissue, epithelial tissue, or a tumor.

27. The system of claim 26, wherein the system is configured to analyze a body fluid that is not blood.

28. The system of claim 1, wherein the body fluid requires pre-processing, concentration or both, before the body fluid is placed into the applicator and wherein the system further comprises a pre-processing device, a concentration device, or both devices.

29. The system of claim 28, wherein the concentration device comprises a centrifuge, a filter, or a cell concentration tube.

* * * * *

UNITED STATES PATENT AND TRADEMARK OFFICE
CERTIFICATE OF CORRECTION

PATENT NO. : 9,602,777 B2  
APPLICATION NO. : 12/768633  
DATED : March 21, 2017  
INVENTOR(S) : James Winkelman et al.

It is certified that error appears in the above-identified patent and that said Letters Patent is hereby corrected as shown below:

In the Claims

Column 24, Line 6, in Claim 1, delete "cells:" and insert --cells;--.

Signed and Sealed this  
Nineteenth Day of September, 2017

Joseph Matal  
*Performing the Functions and Duties of the*  
*Under Secretary of Commerce for Intellectual Property and*  
*Director of the United States Patent and Trademark Office*